(12) United States Patent
Van Derlofske et al.

(10) Patent No.: US 7,258,438 B2
(45) Date of Patent: Aug. 21, 2007

(54) RETINAL FLUX DENSITY METER AND METHOD OF USE

(75) Inventors: John Van Derlofske, Albany, NY (US); Mark Rea, Melrose, NY (US); John Bullough, Troy, NY (US); Andrew Bierman, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 701 days.

(21) Appl. No.: 10/789,506

(22) Filed: Feb. 27, 2004

(65) Prior Publication Data

US 2004/0252275 A1 Dec. 16, 2004

Related U.S. Application Data

(60) Provisional application No. 60/450,546, filed on Feb. 27, 2003.

(51) Int. Cl.
*A61B 3/10* (2006.01)
*A61B 3/02* (2006.01)
*A61B 3/00* (2006.01)
*H05B 41/00* (2006.01)

(52) U.S. Cl. .................. 351/205; 351/200; 351/203; 351/206; 351/212; 351/222; 351/233; 351/243; 351/246

(58) Field of Classification Search ............... 351/200, 351/203, 205, 206, 211–213, 215, 219, 221, 351/222, 233, 239, 243, 246, 163; 359/478, 359/885; 315/324, 151; 607/90

See application file for complete search history.

(56) References Cited

U.S. PATENT DOCUMENTS 3,152,594 A * 10/1964 Kramer ................. 607/90
3,445,153 A * 5/1969 Marks et al. ............... 359/478
4,188,097 A * 2/1980 Holladay ................... 351/243
5,015,924 A * 5/1991 Berman et al. ............. 315/324
5,067,806 A * 11/1991 Kwasman ................... 351/233
7,118,217 B2* 10/2006 Kardon et al. .............. 351/206

OTHER PUBLICATIONS

M. S. Rea, (ed), IESNA Lighting Handbook: Reference and Application 9th ed., (New York: Illuminating Engineering Society of North America),(2000), pp. 1-7, 10-13, Interior 1, Outdoor 1.
R. Mckinley (ed), IES Lighting Handbook (New York: Illuminating Engineering Society) (1947), p. 10-51.
Illuminating Engineering Society, IES Lighting Handbook 2nd ed., (New York: Illuminating Engineering Society (1952), pp. 9-63, 9-68.
J. Kaufman (ed), IES Lighting Handbook 3rd ed., (New York: Illuminating Engineering Society) (1959), pp. 9-76, 9-84.
J. Kaufman (ed), IES Lighting Handbook, 4th ed., (New York: Illuminating Engineering Society) (1966), pp. 9-49, 9-58.

(Continued)

*Primary Examiner*—Loha Ben
(74) *Attorney, Agent, or Firm*—RatnerPrestia

(57) ABSTRACT

A system for approximating flux density of light on a human retina. A housing has an opening allowing light to pass to inside the housing. A baffle coupled to the housing replicates a facial cutoff function response for the light inside the housing. Two detectors are positioned to detect the light inside the housing. One detector produces a photopic spectral response function of the light inside the housing that approximately replicates a spectral response of the foveal cones in the retina. Another detector produces a scotopic spectral response function of the light inside the housing that approximately replicates a spectral response of rods in the retina. A processor coupled to the detectors calculates a mesopic flux density of the light inside the housing based on the photopic and scotopic spectral response functions.

18 Claims, 15 Drawing Sheets

OTHER PUBLICATIONS

J. Kaufman (ed), IES Lighting Handbook 5th ed., (New York: Illuminating Engineering Society) (1972), pp. 9-81, 9-90.

J. Kaufman (ed,) IES Lighting Handbook, Student Reference (New York: Illuminating Engineering Society of North America) (1981), A-3, A-12.

J. Kaufman (ed), IES Lighting Handbook, (New York: Illuminating Engineering Society of North America), Application Volume (1987), pp. 2-5, 2-14.

M. S. Rea, (ed), Lighting Handbook: Reference and Application 8th ed., (New York: Illuminating Engineering Society of North America) (1993), pp. 460, 469.

S. W. Smith, M. S. Rea, "Relationships between Office Task Performance and Ratings of Feelings and Task Evaluations Under Different Light Sources and Levels", Proc. Commission Internationale de l'Eclairage, 19th Session, Kyoto, Japan: Commission Internationale de i'eclairage, (1980) pp. 207-211.

P. R. Boyce, "Human Factors In Lighting", London: Applied Science Publishers, (1981), p. 8.

M. S. Rea, "Essay By Invitation", Light Des. Appl. 26, (1996), pp. 15, 16.

Y. He, M. S. Rea, A. Bierman, J. Bullough, "Evaluating Light Source Efficacy Under Mesopic Conditions Using Reaction Times", J. Illum. Eng. Soc 26 (1997), pp. 125-138.

Y. He, A. Bierman, and M. S. Rea, "A System of Mesopic Photometry", Lighting Res. Technol, vol. 30, No. 4, (1998), pp. 175-181.

M. S. Rea, "The Road Not Taken", Lighting Journal 66, (2001), pp. 18-19, 21-25.

D. A. Palmer, "Standard Observer for Large-Field Photometry at any Level", Journal of the Optical Society of America, vol. 58, No. 9, (1968), pp. 1296-1299.

K. Sagawa, K. Takeichi, "System of Mesopic Photometry For Evaluating Lights in Terms of Comparative Brightness Relationships", Journal of the Optical Society of America, vol. 9, No. 8, (Aug. 1992), pp. 1240-1246.

P. Lonnie, J. Pokorney, V C. Smith, "Luminance", Journal of the Optical Society of America, vol. 10, No. 6, (Jun. 1993), pp. 1283-1293.

Commission Internationale De L'Eclairage, "Mesopic Photometry: History, Special Problems and Practical Solutions", (Vienna: Commission Internationale de L'Eclairage, (1989), pp. II-IV, 1-29.

J. F. VanDerlofske, A. Bierman, M. S. Rea, N. Maliyagoda, "Design and Optimization of a Retinal Exposure Detector", SPIE Proc., vol. 4092, (2000), pp. 60-70.

K. R. Boff, J. E. Lincoln, (ed), Engineering Data Compendium, "Human Perception and Performance", Dayton, Ohio: Armstrong Aerospace Medical Research Laboratory, (1988), pp. 50-53.

H. L. Liou, N. A. Brennan, "Anatomically Accurate, Finite Model Eye For Optical Modeling", Journal of the Optical Society of America, vol. 14, No. 8, (Aug. 1997), pp. 1684-1695.

G. Westheimer, "Image Quality In the Human Eye", Optica Acta, vol. 17, No. 9, (1970), pp. 641-658.

G. Wyszecki, W. S. Stiles, "Color Science", Concepts and Methods, Quantitative Data and Formulae, 2nd Edition, (New York: Wiley), (1982), p. 110.

Commission Internationale De L'Eclairage, "Methods of Characterizing Illuminance Meters and Luminance Meters: Performance, Characteristics and Specifications"(Vienna: Commission Internationale de l'Eclairage), (1987), pp. II-VIII, 1-36.

R. Sekuler, R. Blake, "Perception" 2nd ed., (New York: McGraw-Hill) (1994), p. 84.

M. S. Rea, J. D. Bullough, M. G. Figueiro, "Human Melatonin Suppression By Light: A Case For Scotopic Efficiency", Neuroscience Letters 299, (2001), pp. 45-48.

G. C. Brainard, J. P. Hanifin, J. M. Greeson, B. Byrne, G. Glickman, E. Gerner, M. D. Rollag, "Action Spectrum For Melatonin Regulation In Humans: Evidence For A Novel Circadian Photoreceptor", The Journal of Neuroscience, vol. 21, No. 16, (Aug. 15, 2001), pp. 6405-6412.

K. Thapan, J. Arendt, D. J. Skene, "An Action Spectrum For Melatonin Suppression: Evidence For a Novel Non-Rod, Non-Cone Photoreceptor System In Humans"; Journal of Physiology, 535.1, (2001), pp. 261-267.

D. Sliney, M. Wolbarsht, "Safety With Lasers and other Optical Sources", (New York: Plenum), (1980); p. 338-339.

P. W. Trezona, "Luminance Level Conversions To Assist Lighting Engineers to Use Fundamental Visual Data", Light Res. Technol., vol. 15, (1983), p. 83-88.

M. S. Rea, M. J. Ouellette, "Relative Visual Performance: A Basis For Application", Lighting Res. Technol. vol. 23, No. 3, (1991), pp. 135-144.

J. Van Derlofske, A. Bierman, M. S. Rea, J. Ramanath, J. D. Bullough, "Design And Optimization of a Retinal Flux Density Meter", Institute of Physics Publishing, Meas. Sci. Technol., vol. 13, (2002), pp. 821-828.

* cited by examiner

| Surface | Radius (mm) | Asphericity Q | Thickness (mm) | Refractive Index n (555nm) |
|---|---|---|---|---|
| Anterior Cornea | 7.77 | −0.18 | 0.50 | 1.376 |
| Posterior Cornea | 6.40 | −0.60 | 3.16 | 1.376 |
| Aqueous | NA | NA | NA | 1.336 |
| Anterior Lens | 12.40 | −0.94 | 1.59 | Grad A |
| Mid Lens | Infinity | 1 | 2.43 | NA |
| Posterior Lens | −8.10 | 0.96 | 16.27 | Grad P |
| Vitreous | NA | NA | NA | 1.336 |
| Retina | −10.68 | 1 | NA | NA |

FIG. 4
(Prior Art)

| Surface | Radius of Curvature (mm) | Thickness (mm) | Diameter (mm) | Refractive Index n (at 555nm) |
|---|---|---|---|---|
| Front Lens | 11.46 | 3.9 | 12.0 | 1.457 |
| Rear Lens | Infinite | 0.0 | 12.0 | 1.457 |
| Front Spacer | Infinite | 1.0 | 5.0 | 1.56 |
| Rear Spacer | Infinite | 0.0 | 5.0 | 1.56 |
| Aperture | Infinite | 0.0 | 5.0 | NA |
| Diffuser | Infinite | 0.3 | 12.5 | 1.56 |

FIG. 9
(Prior Art)

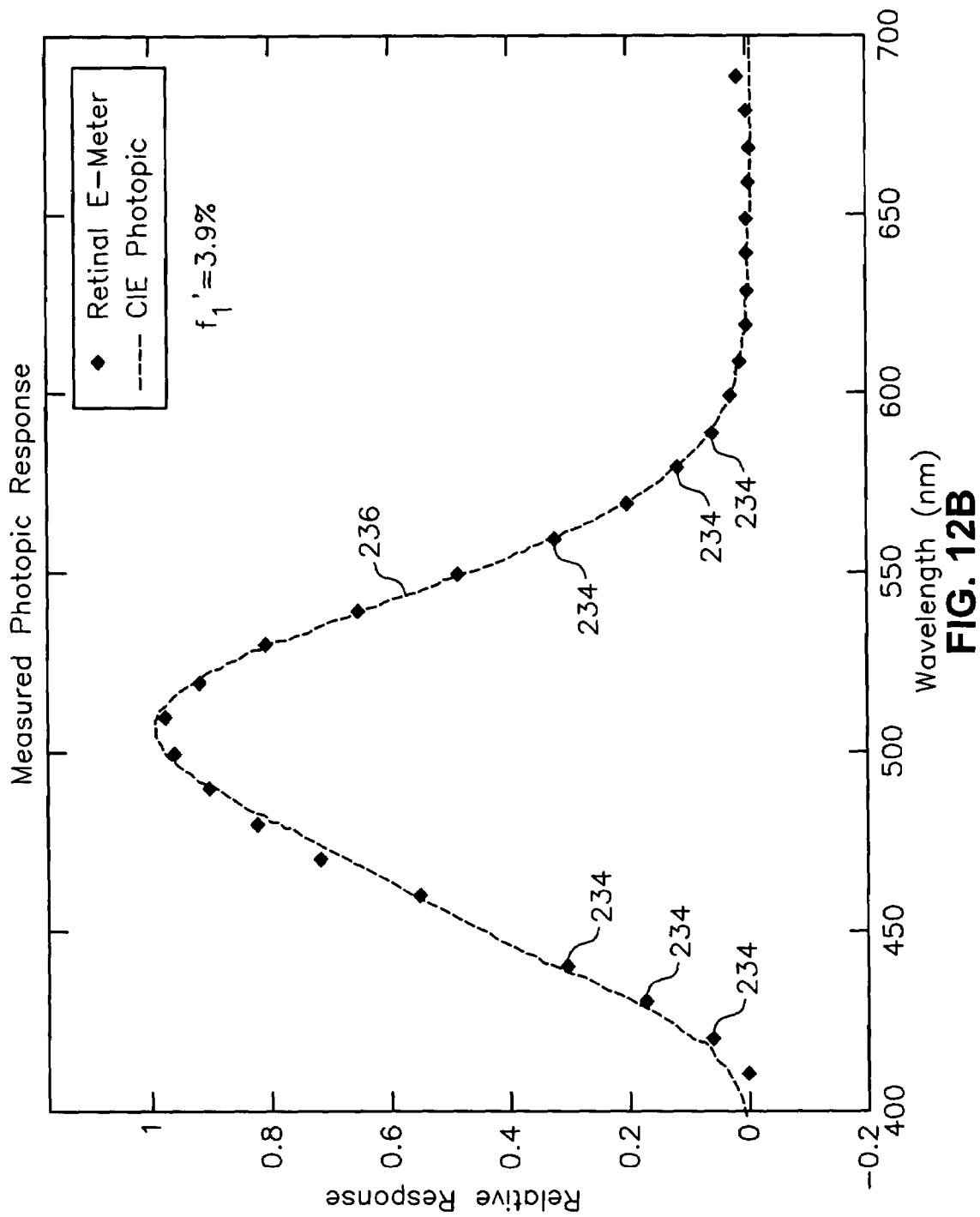

RETINAL FLUX DENSITY METER AND METHOD OF USE

CROSS REFERENCE TO RELATED APPLICATIONS

This application claims the benefit of priority to U.S. Provisional Patent Application Ser. No. 60/450,546, filed on Feb. 27, 2003, the contents of which are incorporated in this application by reference.

FIELD OF THE INVENTION

The present invention relates generally to an illuminance meter and, more particularly, to a retinal flux density meter; that is, an illuminance meter that can approximate flux density on the human retina using both photopic and scotopic spectral responses.

BACKGROUND OF THE INVENTION

Illuminance is the amount of light that falls onto a given area. For example, it is the amount of light that falls per square millimeter. Luminance is the amount of light that is emitted from a given area from a given angle. Luminance has a directional component to it. Luminance is most closely related to brightness and most closely related to what a person sees. Flux density is a measure of illuminance.

Radiometry is the measurement of radiant power at every wavelength across a wide portion of the electromagnetic spectrum. Radiometric measurements are often used to characterize the spectral power distribution of electric light sources. FIG. 1 is a graph with curves showing light source spectral power distributions. Curve 10 shows the spectral power distribution for incandescent lights. Curve 12 shows the spectral power distribution for typical fluorescent lights. Curve 14 shows the spectral power distribution for a white light emitting diode (LED). Radiometric measurements are rarely made outside sophisticated laboratories, however, because accurate radiometric instruments are expensive and impractical for field measurements. Consequently lighting standards and recommendations for offices, schools, factories, etc. are almost never specified in radiometric terms.

Photometry is the measurement of radiation within the visible region of the electromagnetic spectrum using a broadband spectral weighting function, usually the photopic luminous efficiency function ($V_\lambda$). The $V_\lambda$ function was established by the Commission Internationale de l'Eclairage (CIE) in 1924. It is based upon a number of studies of the spectral sensitivity of the human fovea performed in the 1920s. As subsequent research has shown, $V_\lambda$ characterizes the spectral sensitivity of the two most prevalent cone photoreceptor types (L and M cones) in the fovea. In 1924, $V_\lambda$ became part of the international definition of "light."

The CIE also defined in 1951 a scotopic luminous efficiency function ($V'_\lambda$) which represents the spectral sensitivity of rods in the peripheral retina. In 1964, the CIE also published, but did not officially approve, another photopic luminous efficiency function for cone photoreceptors in the peripheral retina out to 10 degrees ($V_{10\lambda}$), which also has proven useful in characterizing the spectral sensitivity of the peripheral retina when cones dominate visual response. FIG. 2 shows these luminous efficiency functions. In FIG. 2, curve 20 illustrates a luminous efficiency function for photopic light in a two degree field; curve 18 illustrates a luminous efficiency function for photopic light in a 10 degree field; and curve 16 illustrates a luminous efficiency function for scotopic light.

In photometry, complete characterization of the spectral power distribution of the light source(s) is reduced to a single number, either illuminance lux or footcandle (lx or fc) or luminance candelas per square meter or footlamberts (cd $m^{-2}$ or fL). When properly calibrated, photometric equipment can provide accurate values within about plus or minus 5% of either illuminance or luminance, depending upon the instrument. Accurate illuminance measurements can be obtained from instruments costing approximately $500 US, whereas similar accuracy for luminance measurements might require an investment of $2000 US because more sophisticated optics are required.

Lighting standards and lighting practices are almost exclusively dominated by illuminance specifications and measurements. Most likely, this reflects the practical and inexpensive nature of the illuminance meters used to measure compliance with the required specifications. Indeed, in the last century, illuminance specifications and measurements were the primary, if not the only, measure of lighting specification and compliance for both indoor and outdoor applications.

Research conducted over the past 50 years has repeatedly shown that $V_\lambda$ is a fairly accurate representation of the spectral sensitivity of the human fovea for such tasks as reading alphanumeric text, threading needles, and visual acuity. This research is discussed in a paper entitled "Relationships between office task performance and ratings of feelings and task evaluations under different light sources and levels," by S. W. Smith et al., published in Proc. Commission Internationale de l'Eclairage, 19$^{th}$ Sess., p. 207 (Kyoto, Japan: Commission Internationale de l'Eclairage) (1980), and in a book entitled "Human Factors in Lighting," by P. R. Boyce, published by Applied Science Publishers (London 1981). Because most tasks performed in offices, factories, and schools require good foveal vision, photometric measurements based upon $V_\lambda$ have been extremely useful in characterizing "light" for visual tasks in interior applications. More significantly perhaps, lighting practitioners have found illuminance measurements useful. It should be emphasized again that the lighting levels in every commercial and industrial building in North America are specified in terms of illuminance. This very high level of acceptance by lighting practitioners reflects the utility of illuminance in characterizing and communicating light levels for interior applications.

Lighting practitioners have not readily accepted illuminance measurements based upon $V_\lambda$, however, as a useful characterization of "light" for outdoor applications. For example, many practitioners have argued that high-pressure sodium (HPS), a yellowish-white lamp that is the dominant light source in outdoor applications, provides poorer visibility at the same illuminance than "whiter" sources like metal halide (MH) or fluorescent. Recent research shows that these observations are valid for some visual tasks but not for others. It seems that, for tasks dominated by foveal vision, illuminance, based on $V_\lambda$, remains a useful characterization of "light" at any light level. For off-axis visual tasks requiring movement detection, however, it is clear that $V_\lambda$ does not characterize the spectral sensitivity of the peripheral retina at low light levels commonly used in outdoor applications. This issue is discussed in a paper entitled "Evaluating light source efficacy under mesopic conditions using reaction times," by Y. He et al., published in J. Illum. Eng. Soc., Vol.

26, page 125 (1997); a paper entitled "A system of mesopic photometry," published in Light. Res. Technol., by Y. He et al., Vol. 30, p. 175 (1998); and in a paper entitled "The road not taken," by M. S. Rea, published in Lighting J., Vol. 66, page 18 (2001).

He et al. have recently developed a model of luminous efficiency based on reaction times to peripheral objects at low, so-called, mesopic levels (discussed below). The development of the model is contained in a paper entitled "Evaluating light source efficiency under mesopic conditions using reaction times," by Y. He et al., published in J. Illum. Eng. Soc., Vol. 26, p. 125 (1997); and in a paper entitled "A system of mesopic photometry," by Y. He et al., published in Light. Res. Technol., Vol. 30, p. 175 (1998). This model differs from brightness-based models in that it models responses mediated by the magnocellular visual channel, which is the same visual channel modeled by $V_\lambda$ at higher luminances and in the fovea.

Brightness-based models are discussed in a paper entitled "Standard observer for large-field photometry at any level," by D. A. Palmer, published in J. Opt. Soc. Am., Vol. 58, p. 1296 (1968); and in a paper entitled "System of mesopic photometry for evaluating lights in terms of comparative brightness relationships," by K. Sagawa et al., published in J. Opt. Soc. Am., Vol. 9, p. 1240 (1992). The visual channel modeled by $V_\lambda$ is discussed in a paper entitled "Luminance," by P. Lennie et al., published in J. Opt. Soc. Am. A, Vol. 10, p. 1283 (1993). Brightness perception, mediated by the parvocellular visual channel, has been found to be distinctly nonadditive for light sources of different spectral power distributions. This is discussed in a report entitled "Mesopic Photometry: History, Special Problems and Practical Solutions" (Vienna: Commission Internationale de l'Eclairage) (1989).

The research by He et al. shows that the spectral sensitivity of the peripheral retina changes with light level over the range of mesopic adaptation conditions, shifting continuously from photopic ($V_{10\lambda}$, which captures the response of the peripheral cones with a peak sensitivity at 555 nm) to scotopic ($V'_\lambda$, capturing the rods' response with a peak sensitivity at 507 nm) sensitivity as light levels are reduced. Depending upon the visual task and the reflectance of the target and its background, the mesopic region corresponds to illuminance levels between approximately 30 and 0.02 lx. Actual nighttime illuminance levels produced by electric light sources are typically between 0.5 and 100 lx. This is shown in a book entitled "Lighting Handbook: Reference and Application," 9$^{th}$ edition, M. Rea (ed.), published by the New York Illuminating Engineering Society of North America (2000 IESNA). Although basic research is useful-in providing scientists with a better understanding of the spectral sensitivity of the human retina at these light levels, research will have little impact on lighting standards or practices until a useful and inexpensive instrument for measuring flux density at mesopic light levels is developed.

A previous device has approximated the spatial efficiency of the eye to determine the total amount of light falling on the retina. This device was discussed in a paper entitled "Design and optimization of a retinal exposure detector," by John Van Derlofske et al., published in SPIE Proc. 4092, p. 60 (2000) (hereinafter "the Van Derlofske paper").

The spatial efficiency function of the eye has two components, the cutoff due to facial structure (brow, nose, and cheek) and the spatial efficiency of the eye itself. A standard cutoff function for facial structure has been published in "Engineering Data Compendium: Human Perception and Performance," by K. R. Boff et al. (ed.), Dayton, Ohio: Armstrong Aerospace Medical Research Laboratory (1988). The spatial efficiency of the eye was determined through computer modeling as discussed in the Van Derlofske paper. A detailed eye model was created in optical modeling software, reproducing all of the important physical and optical properties of the eye. Physical surfaces and volumes modeled include the anterior cornea, the posterior cornea, the aqueous, the anterior lens, the posterior lens, the vitreous, and the retina. Standard optical modeling properties, such as refractive index, surface shape, and thickness, were applied to the model. In addition, other physiological and optical parameters were applied to ensure accuracy. These parameters were determined from the literature or dictated by the assumptions described below.

The pupil diameter was set to 5 mm, chosen as a median diameter. The human pupil ranges on average in diameter from approximately 2 mm, at high light level conditions, to approximately 8 mm at low light levels. The pupil is positioned directly in front of the lens but is not exactly centered with respect to the rest of the eye. It is decentered nasally by about 0.5 mm. Another assumption in eye physiology was made in the area where the muscle attaches to the lens. This area is critical in defining the vignetting or high angle cutoff of the eye. Here the lens edge/muscle tissue area was kept as small as possible while still remaining realistic. This approximation maximized the high angle limit of light acceptance into the eye while retaining physiological accuracy.

Relevant optical properties describing light loss mechanisms in the human eye were also included in the previous model to ensure accuracy. These include the application of Fresnel reflection/transmission and volume attenuation in the eye media. Fresnel reflection/transmission at each surface was used to account for energy loss due to partial reflection. An average volume attenuation value of $\alpha=0.1238$ mm$^{-1}$ (at 555 nm) was used to account for scattering and absorption in the lens as a function of the path length of the incident light. The lens optical densities from which this value was calculated were reported as being from young eyes, although some of those data were from subjects of age up to 45 years. After an age of approximately 30 years, the attenuation coefficient a will increase, but the rate of this increase is greatest for wavelengths shorter than 500 nm due to increased yellowing of the lens. For wavelengths longer than 500 nm, the increased rate of attenuation is much lower, so the value of $\alpha$ is representative for young to middle-aged adults.

The total theoretical spatial efficiency function is shown in FIG. 3 as temporal and brow cross sections on a linear angular scale. Curve 22 illustrates the cross section of the temple to nose and curve 24 illustrates the cross section of the brow to cheek. A linear scale is used so the fine structure and differences in the distributions can be easily seen and compared. The x-axis represents the source angle relative to the eye's optical axis and the y-axis represents the relative amount of flux incident on the retina.

The response curves differ slightly from a cosine distribution. They start slightly narrower than a cosine function at small angles and become slightly wider than a cosine at large angles. The shape of this function is largely dictated by the apparent size of the pupil and by the path length of the light traveling through the ocular media. The sharp cutoff at high angles is mostly due to vignetting or light blocking by the facial structure. Only in the temporal direction, where the facial structure is not a factor, does vignetting in the eye itself become important. Within the eye, vignetting is due to light blocking by the edge of the iris and the lens. The distribution is also slightly shifted in the x dimension due to the nasal shift of the pupil. These differences amount to a discrepancy of up to 6% in the total integrated response for uniform luminance viewing fields compared to a cosine response.

The parameters that were used to model the eye in order to prepare the previous device are shown in FIG. 4. In FIG. 4, the features identified in column 45 are various parts of the eye: row 30 is the anterior cornea; row 32 is the posterior cornea; row 34 is the aqueous; row 36 is the anterior lens; and row 38 is the mid lens. The designation of a mid lens is an imaginary surface that divides the two gradient index regions. Row 40 is the posterior lens; row 42 is the vitreous; and row 44 is the retina.

The columns from column 46 to column 52 identify the parameters used for each feature of the eye. Column 46 is the radius in millimeters; column 48 is the asphericity Q, defined below; and column 50 is the thickness in millimeters of each feature. This thickness is the distance from the identified feature to the surface of the next feature. For example, it is 0.50 mm from the anterior cornea to the surface of the posterior cornea. Column 52 is the refractive index n of each feature of the eye assuming that light at 555 nm is received by the eye.

More specifically, the asphericity Q describes the conic shape of the surface and is defined by, $$y^2+(1+Q)z^2-2zR=0, \quad (1)$$

where z is the distance along the optic axis, y is the perpendicular distance from optic axis, and R is the radius. Grad A (column 52, row 36) and Grad P (column 52, row 40) refer to gradient or nonhomogeneous refractive indices. The index of refraction describes how light refracts, reflects, and propagates in a medium. A gradient index is one that is variable with position in the media. In this case it is given by the equation $$n(w,z)=n_{00}+n_{01}z+n_{02}z^2+n_{10}w^2, \quad (2)$$

where z is again the distance along the optical axis and w is the radial distance perpendicular to the optical axis, or $$w^2=x^2+y^2. \quad (3)$$

For Grad A: $n_{00}=1.368$, $n_{01}=0.049057$, $n_{02}=-0.015427$, and $n_{10}=-0.001978$. For Grad P: $n_{00}=1.407$, $n_{01}=0.00000$, $n_{02}=-0.006605$, and $n_{10}=-0.001978$.

Using the above parameters, an optically and anatomically correct computer model of the human eye was developed in both LightTools® (by Optical Research Associates) and ASAP® (by Breault Research Organization) optical modeling software. Light rays were traced in these models and the retinal illuminance results were used to determine the spatial response function. The more complete ASAP® model includes optical properties such as gradient refractive index and volume attenuation that were not definable in the LightTools® model. FIG. 5 shows a sagital section of the optical axis of the 3D ASAP® model of an eye 60 including the anterior cornea 62, the posterior cornea 64, the aqueous 66, the anterior lens 68, the mid lens 70, the posterior lens 72, the visreous 74, and the retina 76.

Using the parameters defined in FIG. 4, standard optical modeling properties, such as refractive index, surface shape, and thickness, were applied to the model. In addition, other physiological and optical parameters were applied to the ASAP® model to ensure accuracy. These parameters were determined from the literature or dictated by assumptions made.

Relevant optical properties describing light loss mechanisms in the human eye were also included in the model to ensure accuracy. These include the application of Fresnel reflection/transmission and volume attenuation in the eye media. Fresnel reflection/transmission at each surface was used to account for energy loss due to partial reflection. An average volume attenuation value of $\alpha=0.1238$ mm$^{-1}$ (at 555 nm) was used to account for scattering and absorption in the lens and vitreous media as a function of the path length of the incident light.

Once the model was accurately entered into the software and all of the above parameters and properties were assigned, light rays were traced through the systems, using a monochromatic point source with a wavelength of 555 nm. The resulting spatial response function for the eye is shown in FIG. 6 in the x and y planes. More specifically, FIG. 6 illustrates the retinal response as a function of source angle in which curve 78 is the response in the x-plane and curve 80 is the response in the y-plane.

In FIG. 6, the x axis represents the source angle relative to the optical axis and the y axis represents the relative amount of flux incident on the retina. The plotted response curves differ from a cosine distribution. They start slightly narrower than a cosine function at small angles and become slightly wider than a cosine at large angles. The shape of this function is largely dictated by the apparent size of the pupil and by the path length of the light traveling through the ocular media. The sharp cutoff at high angles is due to vignetting or light blocking by the edge of the iris and lens. The distribution is also slightly shifted in the x dimension due to the nasal shift of the pupil.

With the eye's response function calculated from computer simulation and compared to other studies the total eye response function was determined by adding the facial cutoff. A standard facial cutoff function, as described below, was applied in three dimensions to the theoretically calculated retinal response function. The final results of the total retinal response function are shown by x-y slices in FIG. 7, which shows the data in FIG. 3 and links the x direction as the temple-to-nose direction and the y direction as the brow-to-cheek direction. More specifically, FIG. 7 is the retinal response as a function of source angle with facial structure. Curve 82 is the response in the x direction and curve 84 is the response in the y direction.

The computer modeling revealed that the spatial response of the human eye can be roughly approximated as a symmetrical cosine distribution with a highly asymmetrical and presumably sharp cutoff as affected by facial shading. The approach to designing the prior art retinal exposure detector followed the approach used in the computer modeling task by separating the response into that of the eye alone and that due to the effect of the facial shielding. Designing the prior art retinal exposure detector was performed in two steps: (1) designing the facial shading baffle, and (2) designing a detector assembly with a spatial response closely matching that given by the computer model of the eye.

FIG. 8 is a plot of the cutoff angle due to facial shielding based on data contained in a discussion entitled "Optics of the Eye," in Engineering Data Compendium: Human Perception and performance, K. R. Boff et al. (eds.), Section 1.2 (Dayton Ohio: Armstrong Aerospace Medical Research Laboratory (1988) (hereinafter "the Boff reference"). Curve 86 is based on the eye data in the Boff reference. Curve 88 represents the configuration of the baffle used for the previous device. The shape of the baffle needed to produce the appropriate cutoff is made by cutting a sheet of flat material to the shape given by the plot of FIG. 8 and bending it around the cylindrical detector housing. The length, x, and height, y, of the flattened baffle is given by $$x = r \cdot \theta, \; y = \frac{r}{\tan(\phi_c(\theta))}, \quad (4)$$

where r is the radius of the detector housing, $\theta$ is the azimuth angle measured in the direction from cheek to temporal to brow to nose, and $\phi_c(\theta)$ is the cutoff angle. The above equation was derived for a detector located at the center of the detector housing and having no spatial extent, i.e., a point receiver. The above equation specifies the baffle size where the detector is approximately half shaded.

FIG. 8 shows the measured cutoff angle (sensitivity less than 5% of maximum sensitivity) plotted with the desired cutoff angle from the Boff reference. The greatest deviation occurs at the temporal location where the actual cutoff of the eye extends past 90 degrees, yet the retinal exposure detector stops at 90 degrees due to the detector housing itself blocking the light at these large angles. This angular region is relatively unimportant to the total input light, however, because the eye accepts less than 5% of the light at these high angles as shown in FIG. 6.

FIG. 9 lists the component parameters for the previous device. Column 90 and rows 92 to 102 identify the features of the previous device: front lens, rear lens, front spacer, rear spacer, aperture, and diffuser. Columns 104 to 110 identify the parameters for the features identified in each row. Column 104 identifies the radius of curvature; column 106, the thickness, column 108, the diameter; and column 110, the refractive index n at 555 nm. The thickness shown in column 106 is the distance to the next surface. For example, in row 92, 12.0 mm is the distance from the front lens to the next surface of the rear lens. Accordingly, row 92 shows that the front lens has a radius of curvature of 11.46 mm, a thickness of 3.9 mm, a diameter of 12.0 mm, and a refractive index n of 1.457. Rows 94, 96, 98, 100, and 102 show that the radius of curvature of the rear lens, front spacer, rear spacer, aperture, and diffuser are all infinite. That is, they are substantially straight and without any curvature.

Row 94 also shows that the thickness of the rear lens is modeled as 0.0 mm, its diameter is 12.0 mm, and its refractive index is 1.457. Row 96 shows that the thickness of the front spacer is 1.0 mm, its diameter is 5.0 mm, and its refractive index is 1.56. Row 98 shows that the thickness of the rear spacer is 0.0 mm, its diameter is 5.0 mm, and its refractive index is 1.56. Row 100 shows that the thickness of the aperture is modeled as 0.0 mm, its diameter is 5.0 mm, and it has no refractive index. Row 102 shows that the diffuser has a thickness of 0.3 mm, a diameter of 12.5 mm, and a refractive index of 1.56.

The space between the front lens and the diffuser-aperture was filled with optical epoxy so that light would be transmitted from the lens to the diffuser. The purpose of having a space between the lens and the aperture-diffuser is to limit the large angle sensitivity of the detector assembly. A shorter space widens the spatial sensitivity while a longer space narrows the spatial sensitivity. Rays that strike the sides of the spacer are the large angle peripheral rays. Therefore, conduction of these rays to the diffuser increases the sensitivity of the detector assembly for large angles.

FIG. 10 is a cross-sectional view of an existing detector assembly and facial shield. Referring to FIG. 10, tube 138 serves as a housing for the detector. Inside tube 138 is a photocell 130, a photopic filter 128, and a diffuser 126. Two openings 142 and 144 are at the other end of the tube to hold a spacer 124 and a lens 122. Opening 142 defines the aperture of the device and acts like the iris of an eye. Opening 142 allows light to enter the inside of tube 138. Opening 142 has a diameter of 5.0 mm as shown in row 100 of FIG. 9. The characteristics of lens 122 are shown in rows 92 and 94 of FIG. 9. The characteristics of spacer 124 are shown in rows 96 and 98 of FIG. 9. The characteristics of opening 142 and diffuser 126 are shown in rows 100 and 102, respectively, of FIG. 9. The existing assembly also has a facial shield 120 designed as discussed above.

Although not often used by the lighting industry, the CIE established another luminous efficiency function, $V'(\lambda)$, for scotopic, or very low, light levels in 1951. This function applies to large fields (central 20 degrees). In 1964, the CIE produced a provisional photopic function for the central 10 degrees, $V_{10}(\lambda)$, which, again, was not used by the lighting industry. Between photopic and scotopic conditions, spectral sensitivity shifts with light level. No official set of luminous efficiency functions has been established for intermediate, mesopic light levels.

Traditionally, mesopic vision has been assumed to cover the range from 0.001 to 3 cd m$^{-2}$. There are many outdoor applications where light levels fall within this range, such as roadway, parking lot, and security lighting applications. Because there is no official mesopic photometry system recommended by the CIE, only photometers with a $V(\lambda)$ luminous efficiency function are used to measure light at mesopic levels. This practice may produce measured light values with little relationship to the visual effectiveness of the light. Many attempts have been made to measure mesopic luminous efficiency functions and to develop a system of mesopic photometry.

A linear combination model (Equation 5) was proposed by He et al. in a paper entitled "Evaluating light source efficacies under mesopic conditions using reaction times," published in J. Illum. Eng. Soc. 26(1), p. 125-138 (1997) (He I), and in a paper entitled "A system of mesopic photometry," published in Lighting Res. Technol. 30(4), pp. 175-181 (1998) (He II):

$$V_{mes}(\lambda, T_{10}) = k(T_{10})\{x(T_{10})V_{10}(\lambda) + [1 - x(T_{10})]V'(\lambda)\}, \quad (5)$$

where $V_{mes}$ represents the mesopic luminous efficiency as a function of wavelength, $\lambda$, and retinal illuminance, $T_{10}$; $V_{10}$ is the $y_{10}$ function of the CIE 1964 supplementary (10 degrees field) standard observer, which is currently considered the most representative luminous efficiency function for large visual fields at photopic levels and is used here to calculate retinal illuminance, $T_{10}$; $V'(\lambda)$ is the CIE 1951 scotopic luminous efficiency function; x is the adaptation coefficient, which depends upon the photopic retinal illuminance of the reference light and varies between 0 and 1; and k is a normalization constant.

The relationship between the adaptation coefficient x and retinal illuminance is described by the following function using a least-squares solution in He II:

$$x(T_{10}) = 0.0477T_{10} + 0.004 \quad (6)$$

He II developed the following algorithm. The lower limit for the photopic vision can be estimated from Equation 6 by equating x to 1 and calculating the value of $T_{10}$.

The value of x in Equation 6 is defined in terms of the photopic retinal illuminance of the reference light (589 nm in the He II experiment). Adaptation under mesopic conditions cannot be characterized by photopic trolands alone but should be determined by the excitation of rods and cones and, implicitly, lateral inhibition of rods by cones. Although the physiology of this interaction is not entirely clear, it must be true that the adaptation coefficient, x, is dependent on the adaptation spectrum as well as flux density on the retina. Ideally, Equation 6 should be defined in terms of mesopic trolands, $T_{mes}$, which would characterize the true mesopic adaptation level and therefore would be independent of a particular reference source.

A function relating $x(T_{mes})$ to $T_{mes}$ can be determined using a least-squares method. This function is described by Equation 7:

$$x(T_{mes}) = 0.115(T_{mes} + 0.006)^{0.71} \text{ for } T_{mes} < 21$$

$$x(T_{mes}) = 1 \text{ for } T_{mes} \geq 21 \quad (7)$$

Equation 7 can be generally applied to any adapting spectrum and light level. The following computational procedure illustrates the approach disclosed in He II by which mesopic light level can be evaluated for any light source spectra.

(a) Measure the photopic luminance L (in cd m$^{-2}$) for the spectral radiance distribution $L_e(\lambda)$ (in W m$^{-2}$sr$^{-1}$).
(b) Calculate the pupil size A (in mm$^2$) of an average observer under L using the following equation adapted from a paper entitled "Luminance level conversions to assist lighting engineers use fundamental visual data," by P. Trezona, published in Lighting Res. Technol. 15(2), p. 83-88 (1983):

$$A = [5 - 3 \tan h(0.41 \log(L))]^2 / 4 \quad (8)$$

or from a paper entitled "Relative visual performance: A basis for application," by M. S. Rea et al., published in Lighting Res. Technol. 23(3), p. 135-144 (1991):

$$A = [4.77 - 2.44 \tan h(0.31 \log(L))]^2 / 4 \quad (8')$$

(c) Calculate the retinal illuminance $T_{10}$ (in photopic Td) and use $T_{10}$ as an initial value for $T_{mes}$:

$$T_{10} = AKL_e(\lambda) V_{10}(\lambda) d\lambda \quad (9)$$

where K=683 lm W$^{-1}$.
(d) Calculate the value of $x(T_{mes})$ using Equation 7.
(e) Use the value of $x(T_{mes})$ in Equation 10 to determine a mesopic luminous efficiency function $V_{mes}(\lambda, T_{mes})$:

$$V_{mes}(\lambda, T_{mes}) = [x(T_{mes}) V_{10}(\lambda) + (1 - x(T_{mes})) V(\lambda)] \quad (10)$$

(f) Calculate the retinal illuminance $T_{mes}$ (in mesopic T):

$$T_{mes} = AK_{mes} L_e(\lambda) V_{mes}(\lambda, T_{mes}) d\lambda \quad (11)$$

where $K_{mes}$ is a scaling factor equal to $683/V_{mes}(\lambda=555$ nm) lm W$^{-1}$.
(g) Use the resulting value of $T_{mes}$ in Equation 7 and repeat the steps in Equations 8 through 11 until changes in $T_{mes}$ are negligible.
(h) Calculate the mesopic luminance $L_{mes}$:

$$L_{mes} = T_{mes}/A \quad (12)$$

To overcome the shortcomings of the existing detector, a new retinal flux density meter is provided. An object of the present invention is to make an optical system that mimics or approximates the light-collecting abilities of the eye. A related object is to create a meter that approximates the amount of light that enters into an eye, rather than approximating only the light that falls onto the plane of an eye. Another object is to provide a meter that measures the photopic and scotopic spectral responses of light incident upon the meter. It is still another object of the present invention to provide a method of approximating mesopic illuminance or flux density on the eye.

SUMMARY OF THE INVENTION

To achieve these and other objects and in view of its purposes, the present invention provides a system for approximating flux density of light on a retina. The system comprises a housing having an opening allowing light to pass to an inside of the housing. It also has a baffle coupled to the housing. The baffle replicates a facial cutoff function for the light passing to the inside of the housing. The system also has two detectors positioned to detect the light inside the housing. One detector produces a photopic spectral response function of the light inside the housing that approximately replicates a spectral response of foveal cones. The other detector produces a scotopic spectral response function of the light inside the housing that approximately replicates a spectral response of rods in the retina.

A processor is coupled to the detectors. The processor is configured to calculate a flux density of the light inside the housing based on the photopic and scotopic spectral response functions.

The invention also provides a method of approximating a peripheral-photopic luminance of light incident on a combination of foveal and peripheral cones of a retina. One step of the method is producing a first signal that is weighted by a spectral response of the foveal cones to the light and proportional to a first flux density of the light received by the foveal cones. Another step of the method is producing a second signal that is weighted by a spectral response of rods in the retina to the light and proportional to a second flux density of the light received by the rods. A third step of the method is applying a function to the first and second signals to approximate the peripheral-photopic response.

The invention also provides a method of approximating a mesopic retinal flux density of light incident on a combination of cones and rods of a retina. The first step of the method is producing a first signal that is weighted by a spectral response of the cones to the light and proportional to a first flux density of the light received by the cones. A second step of the method is producing a second signal that is weighted by a spectral response of the rods to the light and proportional to a second flux density of the light received by the rods. A third step of the method is applying an algorithm to the first and second signals to determine the mesopic retinal flux density.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 4 is a table showing the parameters used to model the eye;

FIG. 9 is a list of the component parameters for an existing device;

FIG. 12B is a graph including curves illustrating the relative measured scotopic response of the meter illustrated in FIG. 11A.

DETAILED DESCRIPTION OF THE INVENTION

The invention described below is a meter that approximates retinal flux density. That is, it approximates the density of light falling on the retina of an eye. In an exemplary embodiment, the meter may be made small enough to be easily portable.

Figure 11A:
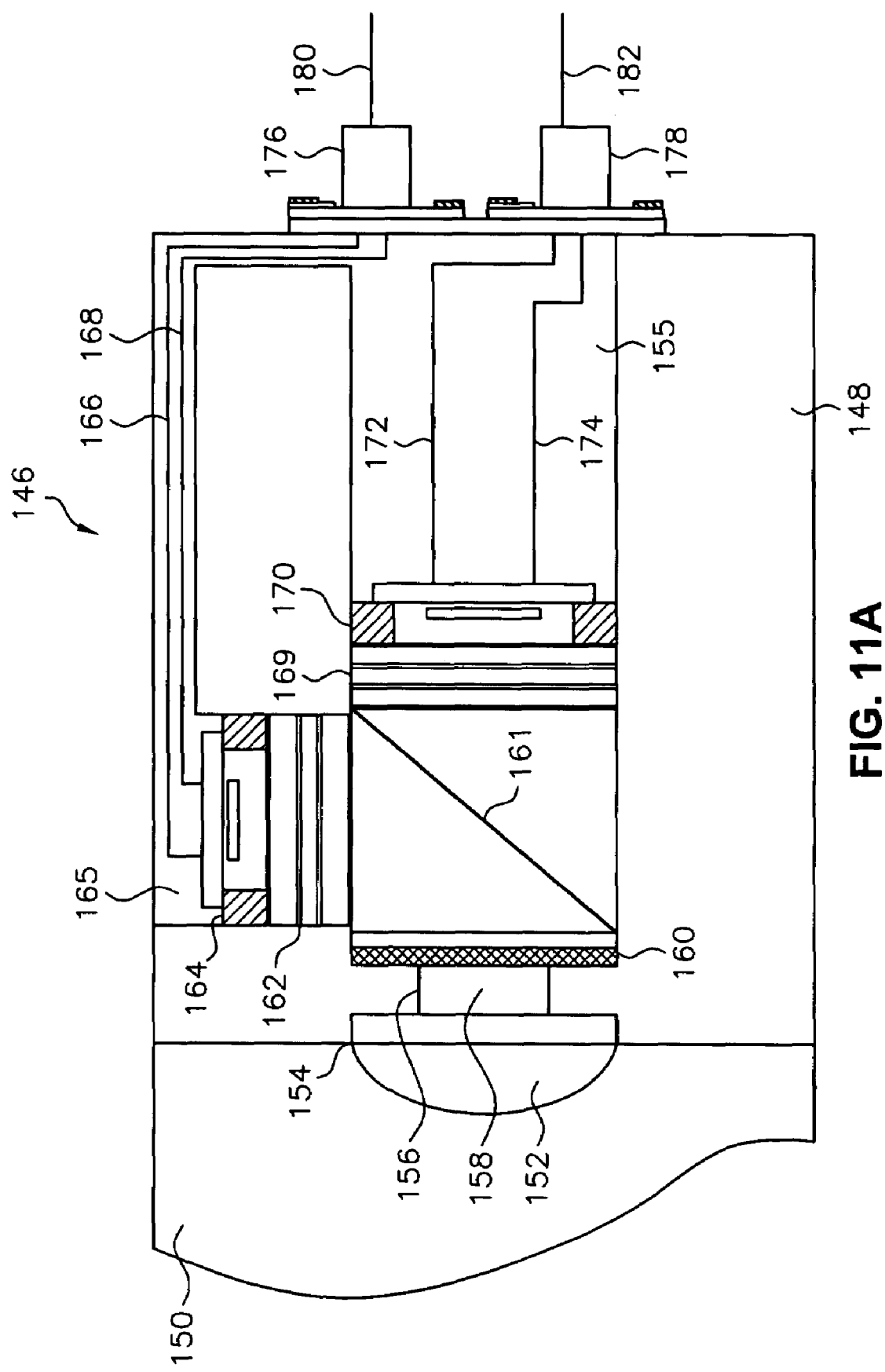
FIG. 11A is a cross sectional view of a retinal flux density meter according to an exemplary embodiment of the invention.

A schematic diagram of retinal flux density (RFD) meter 146 is shown in FIG. 11A. The RFD meter 146 shown in FIG. 11A includes a cylindrical housing 148, a cylindrical baffle 150, a lens 152, a decentered aperture 154, an optical diffuser 160, a beam splitter 161, a photopic filter 169, a scotopic filter 162, and two silicon photodiodes or other photocells 164, 170.

Photopic filter 169 and scotopic filter 162 may be coupled to their own photocells 170 and 164, respectively. In an exemplary embodiment, photocell 164 may be behind filter 162 and photocell 170 may be behind filter 169. In an alternative embodiment, photocells may be developed that have the same response curves as those provided by filters 162 and 169. In that alternative, filters 162 and 169 may be eliminated.

In an exemplary embodiment, housing 148 may be a cylindrical tube full of black polycarbonate plastic. When the tube is made of black plastic, the inside of the tube may also be black to minimize stray light bouncing around inside the tube. In an alternative embodiment, the tube may be made in other shapes and colors as long as stray light is minimized. In an exemplary embodiment, a first opening 155 may be provided in one end of housing 148 and a second opening 165 may be provided in a side of housing 148.

Figure 1:
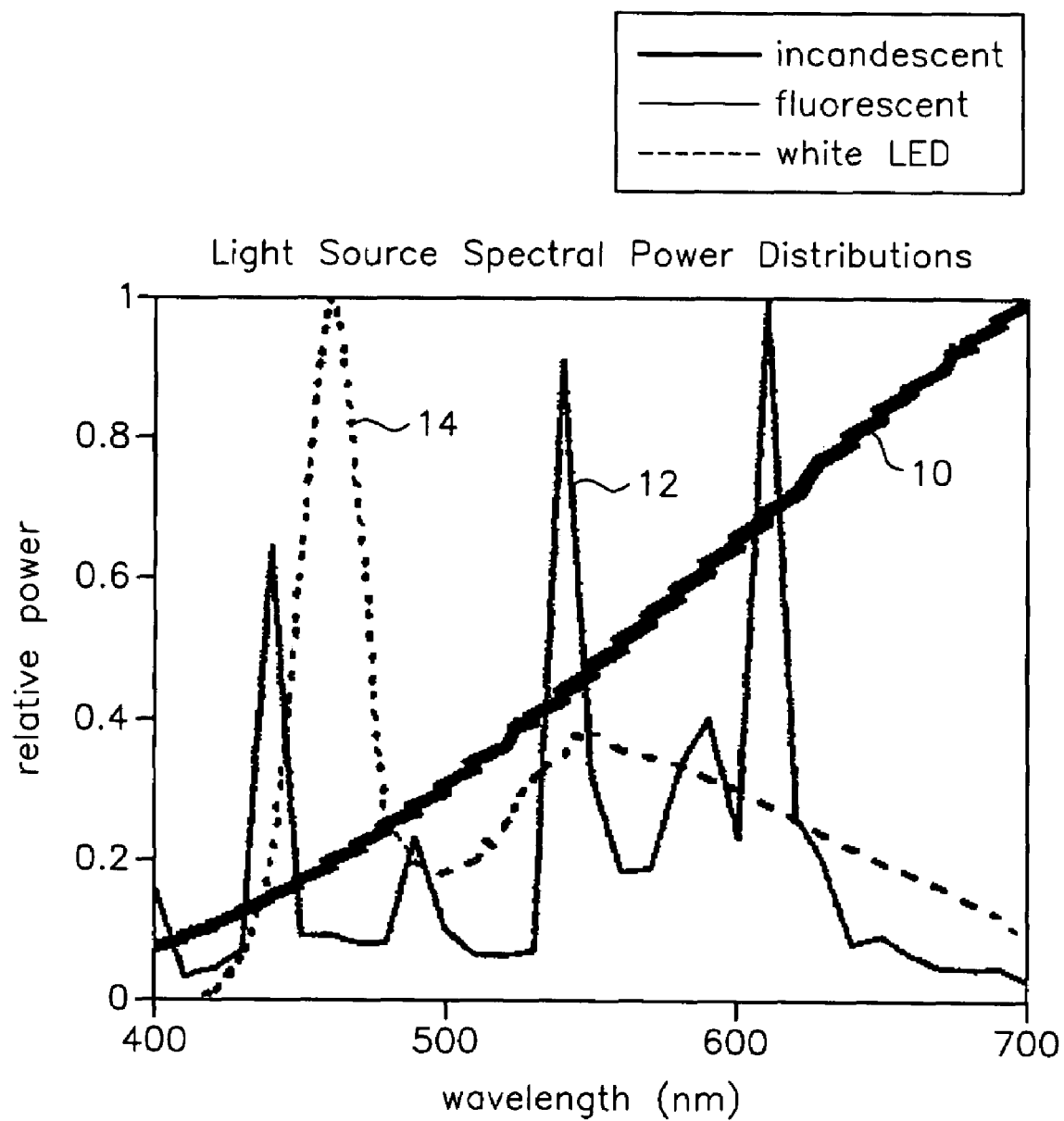
FIG. 1 is a graph with curves showing light source spectral power distributions.
Figure 2:
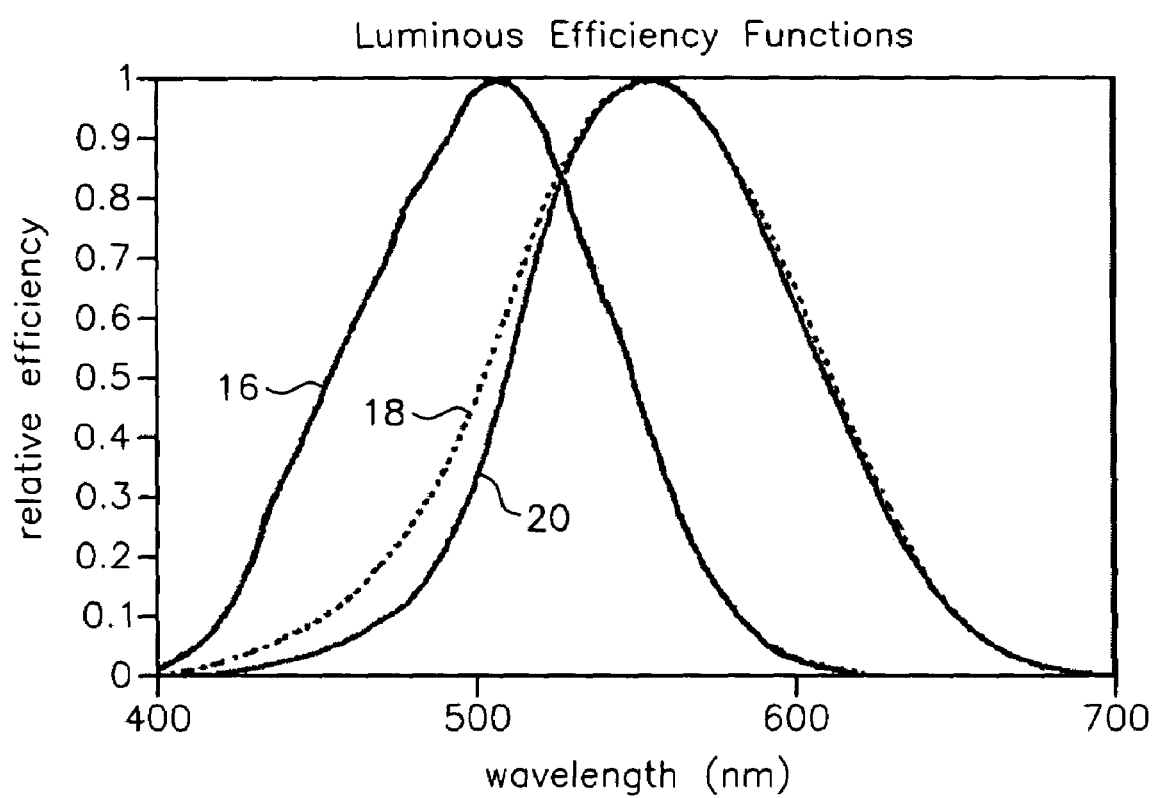
FIG. 2 is a graph with curves showing luminous efficiency functions promulgated by the Commission Internationale de l'Eclairage.
Figure 3:
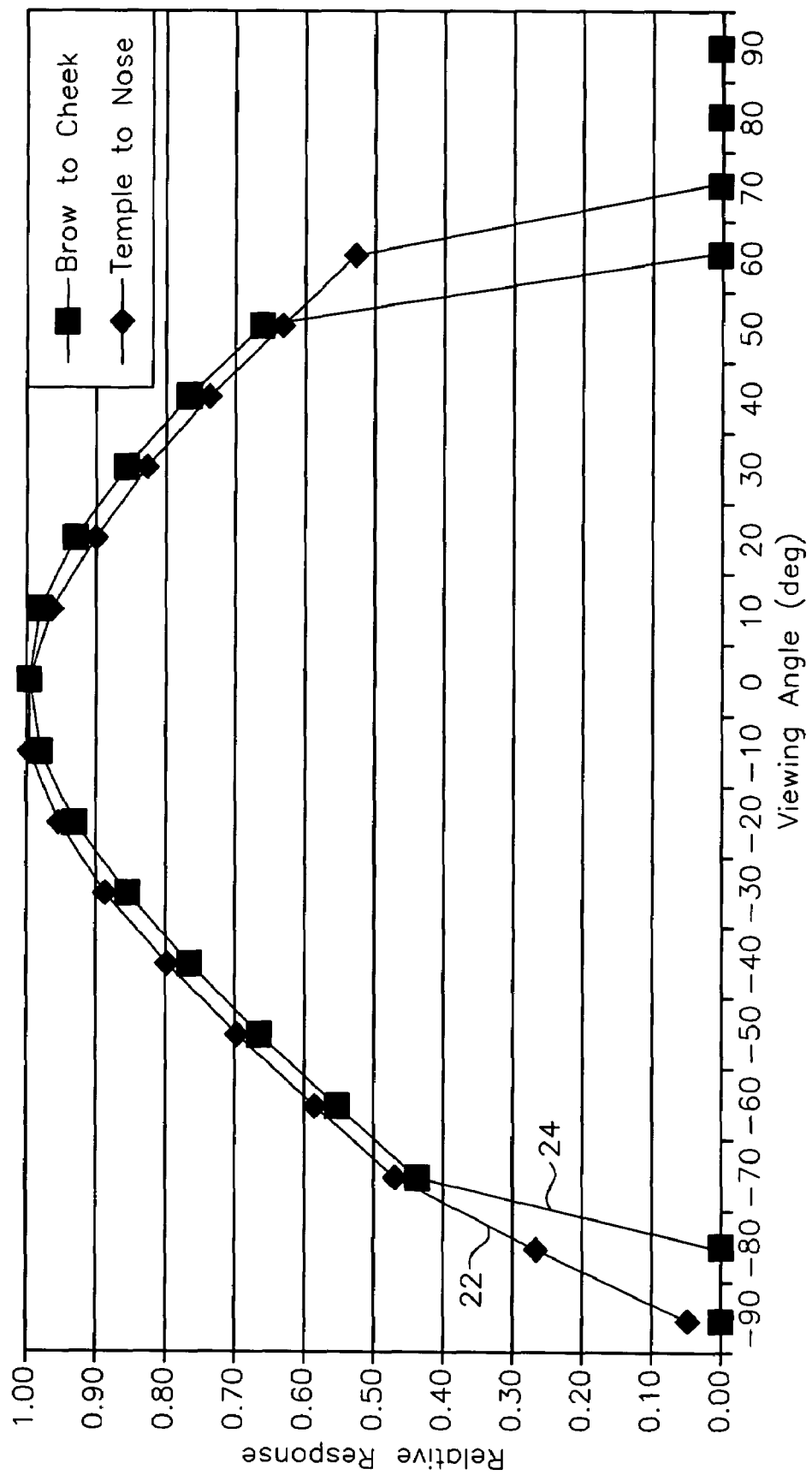
FIG. 3 is a graph with curves showing the total theoretical spatial efficiency function as temple and brow cross sections on a linear angular scale.
Figure 5:
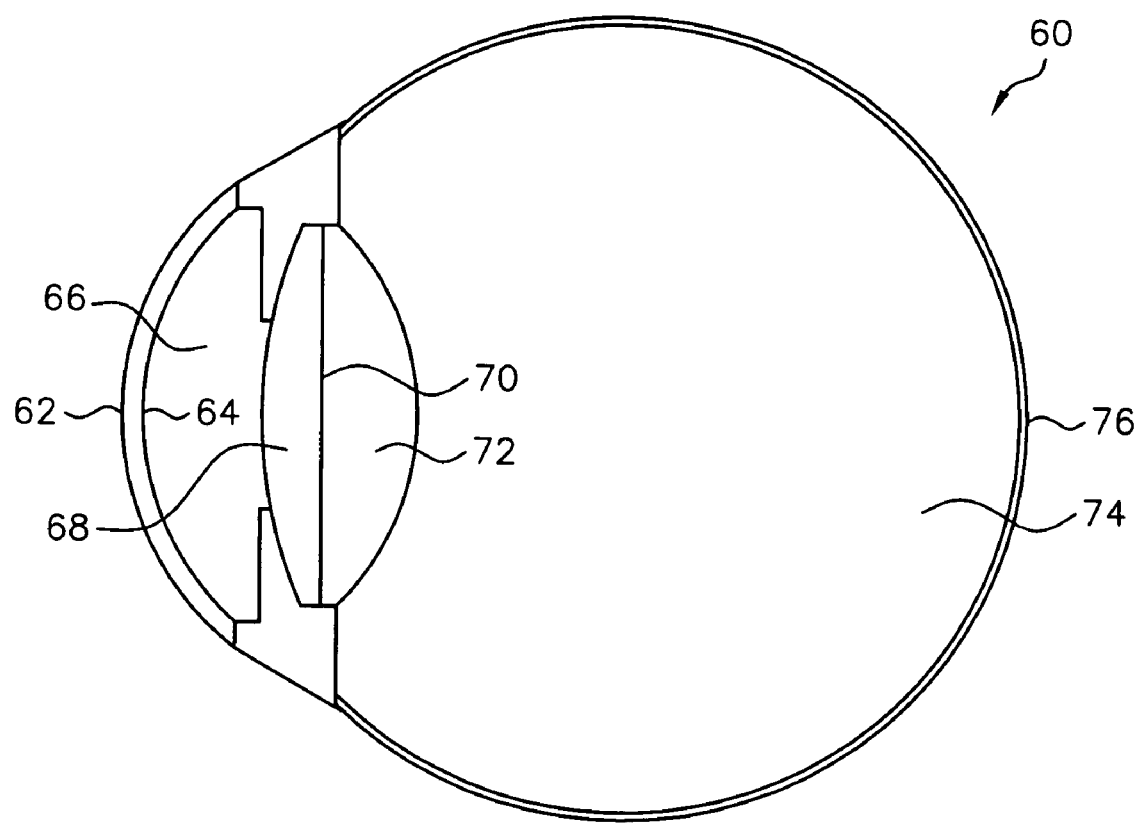
FIG. 5 is a sagital section of the optical axis of a 3D ASAP® model of the eye.
Figure 6:
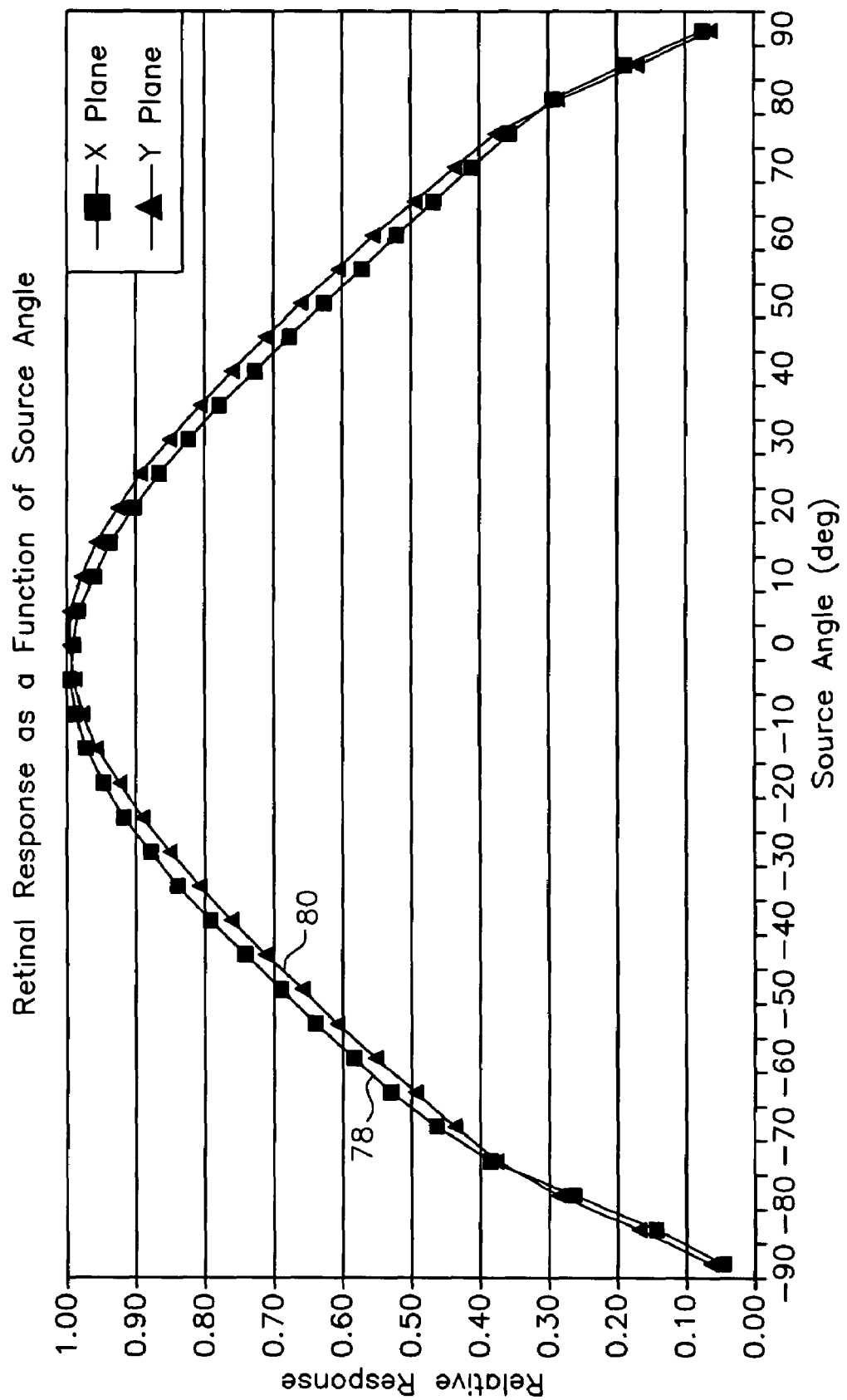
FIG. 6 illustrates the retinal response as a function of source angle.
Figure 7:
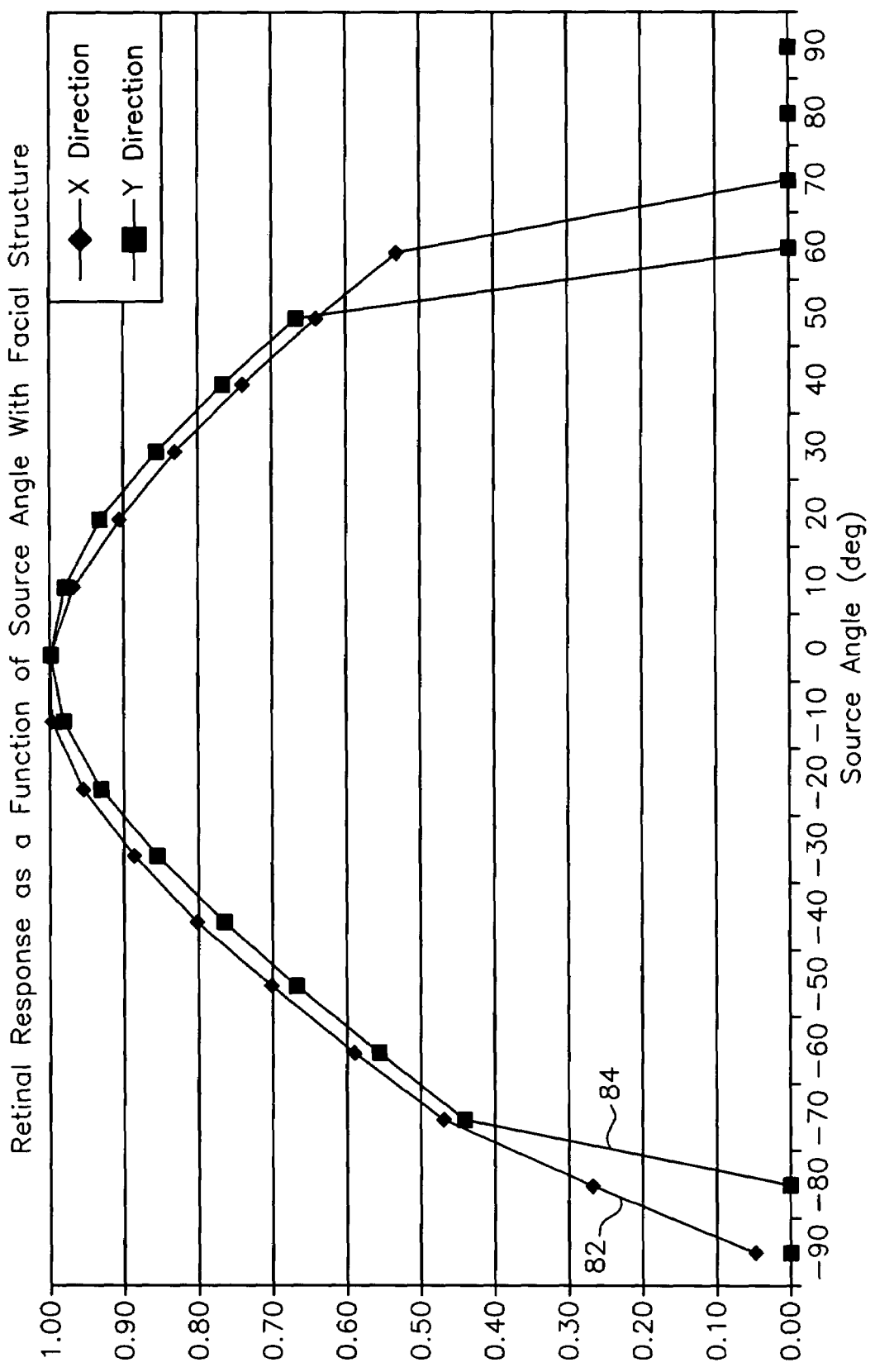
FIG. 7 illustrates the retinal response function as a function of source angle with facial structure.
Figure 8:
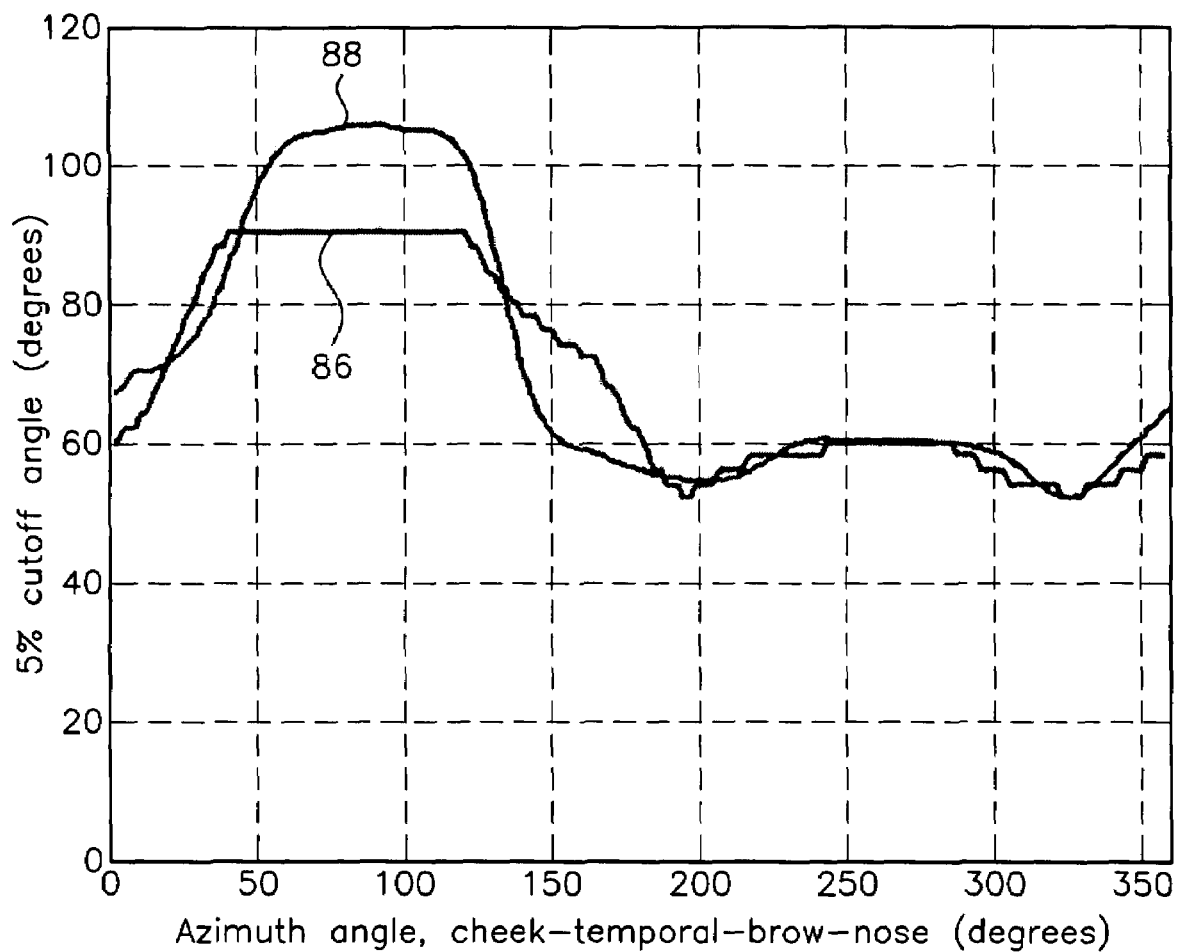
FIG. 8 is a plot of the cutoff angle due to facial shielding.

Baffle 150 may also be cylindrical, may also be black, and may be made with the same characteristics as the baffle depicted in FIG. 8. Baffle 150 mimics the physiology of the face based upon an average function for an eye, an eyebrow, a nose, and a cheek. Baffle 150 may be made black to minimize the light that may bounce off baffle 150. Baffle 150 extends out past the body of the plastic housing 148 and the lens 152. When the exemplary cylindrical baffle 150 is used, lens 152 may be approximately in the middle of baffle 150 and baffle 150 may encircle lens 152. The distance that baffle 150 extends beyond the plastic housing 148 is related to the diameter of the tube. In an exemplary embodiment, the diameter of the tube and baffle 150 may be about 50.8 mm.

Figure 10:
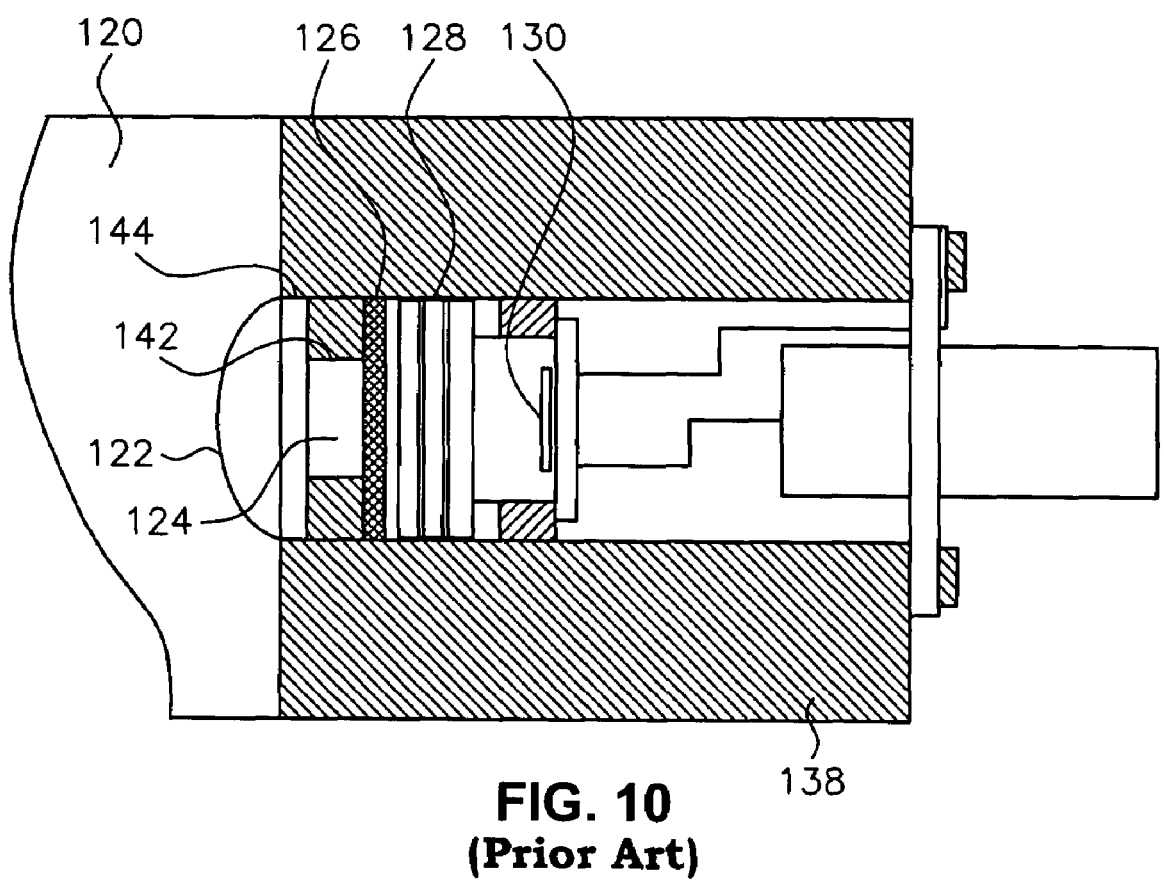
FIG. 10 is a cross-sectional view of an existing detector.

Many of the components of meter 146 illustrated in FIG. 11A may be the same as the elements shown in FIG. 10 with the same parameters listed in FIG. 9. Specifically, in an exemplary embodiment, lens 152, spacer 158, aperture 156, and diffuser 160 in FIG. 11A may have the same characteristics as those shown in FIGS. 9 and 10 for the same reasons that were discussed regarding FIGS. 9 and 10. The dimensions and parameters shown in FIG. 9 are examples of the features of the invention that are included to more clearly demonstrate the overall nature of the invention. These examples are exemplary, not restrictive, of the invention. Other dimensions and parameters may be used. In an exemplary embodiment, lens 152 may be a fused silica lens. In an alternative embodiment, lens 152 may be any other glass, plastic, or ceramic material.

Aperture 156 is referred to as the aperture in row 100 of FIG. 9. Aperture 156 acts like an iris of the eye. It defines the aperture size which, in turn, determines the amount of light that enters the inside of the tube. Adjacent lens 152 and spacer 158 is diffuser 160.

A detector mechanism is positioned inside housing 148 to detect the light inside housing 148. The detector mechanism includes scotopic filter 162, photocell 164, photopic filter 169, and photocell 170. The detector mechanism is positioned inside housing 148 to detect the light inside housing 148. The detector mechanism produces a photopic spectral response function of the light inside the tube that approximately replicates a spectral response function of cones in the central retina. The detector mechanism also produces a scotopic spectral response function of the light inside the tube that approximately replicates a spectral response of rods in the retina.

The detector mechanism includes a first detector and a second detector. The first detector may produce the photopic spectral response function. The second detector may produce the scotopic spectral response function. The first detector may include a first filter which is the photopic filter 169. The first detector may also include a first photocell which is the photocell 170. The second detector may include a second filter which is scotopic filter 162. The second detector may also include a second photocell 164. Scotopic filter 162 and photocell 164 may be inserted into housing 148 from the top through opening 165. Photopic filter 169 and photocell 170 may be inserted into housing 148 from the right side through opening 155. In an exemplary embodiment, photocells 164 and 170 may each be the same kind of photocell. In an alternative embodiment, photocells 164 and 170 may be different.

Although FIG. 11A shows a relatively large distance between the right end of housing 148 and photocell 170, the distance may be less. Similarly, the distance that photocell 164 is inserted into housing 148 may be more or less than the distance illustrated. An important consideration in determining the placement of photocells 164 and 170 is that they be located completely within the material of housing 148.

FIG. 11A shows an exemplary embodiment in which photopic filter 169 and photocell 170 are placed vertically and scotopic filter 162 and photocell 164 are placed horizontally. In an alternative embodiment, the placement of the filters and their photocells may be reversed. That is, photopic filter 169 and photocell 170 may be placed horizontally while scotopic filter 162 and photocell 164 may be placed vertically. In yet another embodiment, the filters and photocells do not have to be vertical or horizontal. They may be placed at other angles within housing 148. Furthermore, although FIG. 11A shows a filter and photocell as placed from the top of housing 148, they may alternatively be placed from the side or from the bottom. If the orientation of these elements is changed, the beam splitter may be rotated in order to properly divide the incoming light.

Aperture 156 may be smaller than openings 155, 165. Aperture 156 is provided in housing 148 to enable spacer 158 to be inserted into opening 154.

In an exemplary embodiment, photocells 164 and 170 are round, provide substantially linear responses, and can respond to low levels of light. In an exemplary embodiment, photocells 164 and 170 may have a different shape. Regardless of their shape, they may be able to respond to 0.0001 lx of light.

The facial cutoff is approximated by the cylindrical baffle or facial shield that encompasses the entire input face of the detector. As discussed above, the baffle replicates the retinal spatial response for the light passing to the inside of the tube. The aperture 156 and fused silica lens 152 are used to reproduce the spatial luminous response of the eye itself. Aperture 156 may have a 5 mm diameter and may be offset nasally by 0.5 mm from the optical axis. The 5 mm diameter of aperture 156 may be selected as a compromise between increased flux acceptance for a large diameter pupil, 8 mm, and increased baffle shading accuracy for a small diameter pupil, 2 mm. In practice, a scaling factor may be calculated for changing pupil size at a given light level and applied to the other measurement values. In an alternative embodiment, the diameter of the aperture need not be 5 mm.

The detector mechanism also includes optical diffuser 158 which may be used to uniformly fill the silicone photodiodes with light and integrate light at all angles within the solid acceptance angle of the detector. In an exemplary embodiment, the diameter of diffuser 158 may be 12.5 mm. That is, the diameter of diffuser 158 may be the same as the diameter of lens 152. In an alternative embodiment, the diameter of diffuser 158 need not be the same diameter as lens 152. It may be slightly larger than the diameter of aperture 156 and spacer 158. In another embodiment, the diameter of diffuser 158 may be the same as the diameter of spacer 158 and aperture 156.

The detector mechanism also includes beam splitter 161. In an exemplary embodiment, beam splitter 161 may be round and may be glued to the walls of housing 148. In an alternative embodiment, beam splitter 161 may have a different shape. Also in an exemplary embodiment, beam splitter 161 may be approximately 70% reflective and approximately 30% transmissive. That is, in an exemplary embodiment, approximately 70% of the input light coming into housing 148 through lens 152, aperture 156, and spacer 158 may be transmitted to scotopic photocell 164 by being reflected up to scotopic photocell 164. Approximately 30% of the input light may be transmitted to photopic photocell 170.

In an exemplary embodiment, more light may be sent to the scotopic channel due to the higher total absorbance of scotopic filter 162 and the low light levels typically associated with scotopic measurement. In an alternative embodiment, beam splitter 161 may divide the light differently than 70-30. For example, it may divide the light 50-50, or any other percentage, as long as enough light is transmitted to each photocell to enable each photocell to provide a sufficient output signal that can be accurately measured.

The detector assembly geometry described above allows for the nearly simultaneous photopic and scotopic measurements. A weighted illuminance that closely approximates the $V_{10\lambda}$ spectral response of the peripheral retina under photopic conditions can be calculated through post processing of the scotopic and photopic values. Also through post processing, mesopic illuminance can be calculated, depending on the absolute light level. This is done through an iterative process of adding proportions of the photopic ($V_\lambda$) and scotopic ($V'_\lambda$) results based on, but different from, the algorithm described by He II.

Figure 12A:
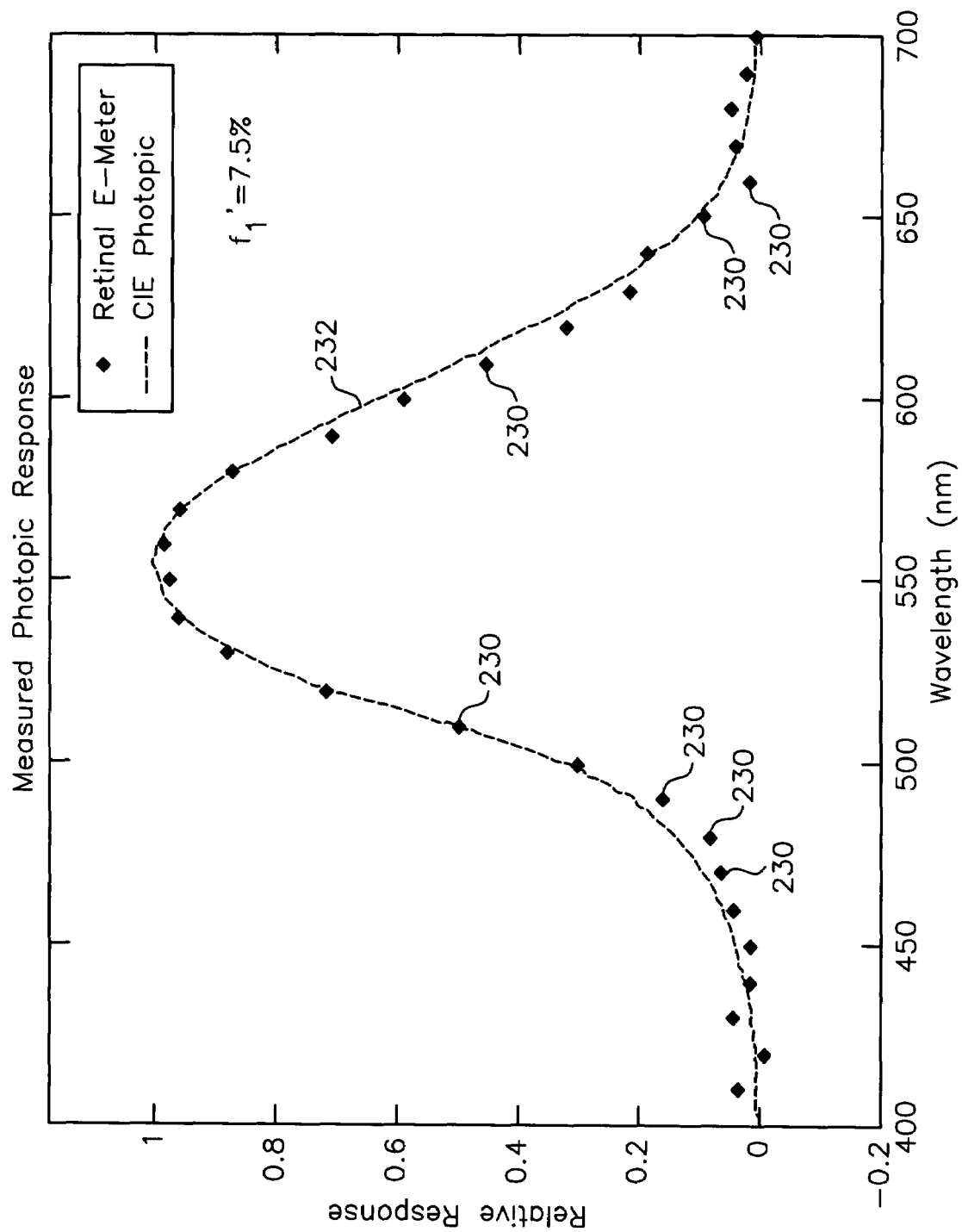
FIG. 12A is a graph including curves illustrating the relative measured photopic response of the meter illustrated in FIG. 11A.

The photopic filter 169 with its photopic photocell 170, and the scotopic filter 162 with its scotopic photocell 164, comprise two separate detectors. The photopic detector approximates the CIE $V_\lambda$ efficiency function. The scotopic detector approximates the CIE $V'_\lambda$ efficiency function. The photopic and scotopic responses are shown in FIGS. 12A and 12B along with corresponding standard functions. More specifically, the response indicated by dots 230 in FIG. 12A illustrates the relative measured photopic response of photopic filter 169 of meter 146 illustrated in FIG. 11A. Response dots 230 illustrate the relative response of photopic filter 169 shown in FIG. 11A to light of various wavelengths. For example, photopic filter 169 may not allow light having a wavelength of about 400 nm or light having a wavelength of about 700 nm to be transmitted through it to photocell 170. On the other hand, photopic filter 169 may allow the maximum amount of light to be transmitted to photocell 170 when the light has a wavelength of about 550 nm.

Curve 232 in FIG. 12A is the standard photopic function promulgated by the CIE. An $f_1'$ number has been defined by the CIE in a paper entitled "Methods of Characterizing Illuminance Meters and Luminance Meters: Performance, Characteristics and Specifications" (Vienna: Commission Internationale de l'Éclairage) (1987). The value of $f_1'$ quantifies the deviation of the measured response functions from the standard CIE functions as a weighted percentage of the absolute values of area differences under the functional curves. The value of $f_1'$ for photopic filter 169 of RFD meter 146 is shown in FIG. 12A to be 7.5%.

The response indicated by dots 234 in FIG. 12B illustrates the relative measured scotopic response of meter 146 illustrated in FIG. 11A. Response dots 234 illustrate the relative response of scotopic filter 162 shown in FIG. 11A to light of various wavelengths. For example, scotopic filter 162 may not allow light having a wavelength of about 400 nm or light having a wavelength of about 700 nm to be transmitted through it to photocell 164. On the other hand, scotopic filter 162 may allow the maximum amount of light to be transmitted to photocell 164 when the light has a wavelength of about 500 nm. Curve 236 in FIG. 12B is the standard scotopic function promulgated by the CIE. The value of $f_1'$ for scotopic filter 162 of RFD meter 146 is shown in FIG. 12B to be 3.9%.

In an alternative embodiment, the values of $f_1'$ may be different depending upon the quality of the materials that are used and the optical design that may be used.

As can be seen in FIGS. 12A and 12B, one difference between scotopic filter 162 and the photopic filter 169 is the amount of light that each filter allows to pass through. A second difference is the specific wavelength that is allowed to pass through each filter. For example, photopic filter 169 allows through the most light at about 555 nm; while scotopic filter 162 allows through the most light at about 507 nm. The combination of each filter with its respective photocell provides the responses illustrated in FIGS. 12A and 12B. That is, the photocells transmit signals based upon the wavelength of the light that the filters allow to pass and also based upon the quantity or brightness of the light.

Accordingly, for example, there may be twice as much light of exactly the same wavelength at one time than the amount of light at an earlier time. The photocells would indicate that the quantity of light is double. But the ratio between the photopic and scotopic responses would not change, as long as the filters were not changed. In effect, the filters perform a weighting of the light (flux) incident on the detector so that one of the photocells transmits a signal proportional to a first retinal flux weighted by the photopic spectral response and the other transmits another signal proportional to a second retinal flux weighted by the scotopic spectral response.

Light that is incident on meter 146 may be filtered by filters 162 and 169 which transmit the light in accordance with the response curves shown in FIGS. 12A and 12B. The quantity of light which passes through the filters may then be measured by their respective photocells 164 and 170. As the filters of RFD meter 146 transmit the photopic and scotopic responses for a range of light wavelengths at given light levels, their respective photocells convert the light into current signals in a way that is known to those skilled in the art.

Accordingly, the light from each filter is a weighted amount light that is weighted by the spectral response of each filter. When the light from each filter is incident upon its respective photocell, each photocell produces output current signals that are proportional to the weighted amount of light. The output current signals may change as the weighted amount of light changes. That is, photopic photocell 170 may produce output current signals that are proportional to the weighted amounts of light that are incident upon photocell 170 from photopic filter 169. The signal from photocell 170 is proportional to the retinal flux weighted by photopic spectral response function. Similarly, scotopic photocell 164 may produce output current signals that are proportional to the weighted amounts of light that are incident upon photocell 164 from scotopic filter 162. The signal from photocell 164 is proportional to the retinal flux weighted by the scotopic spectral response function.

Each of the output current signals may be proportional to flux density. Thus, a current signal produced by photopic photocell 170 may be proportional to photopic flux density. Furthermore, because meter 146 has been designed to mimic or approximate features of an eye and features surrounding an eye, a current signal produced by photopic photocell 170 may be proportional to photopic retinal flux density (E). Similarly, a current signal produced by scotopic photocell 164 may be proportional to scotopic flux density and, therefore, proportional to scotopic retinal flux density (E'). Values of E and E' may be expressed as lumens per square meter ($lm/m^2$).

Current signals from photopic photocell 170 may be transmitted over wires 172, 174 to a connector 178. Current signals from scotopic photocell 164 may be transmitted over wires 166 and 168 to a connector 176. Based on the signals from the photocells, the invention can determine how much light is incident upon meter 146.

Figure 11B:
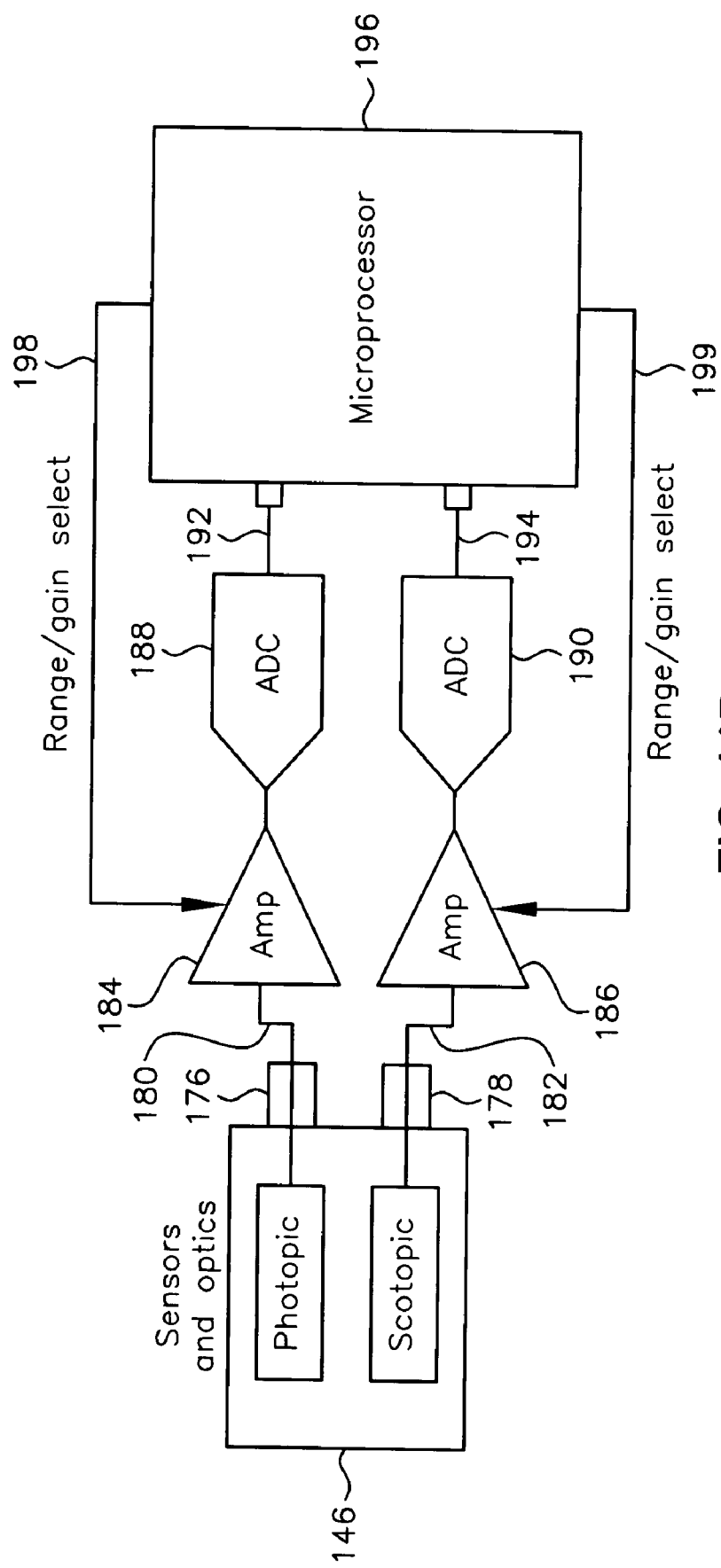
FIG. 11B is a schematic diagram of a system for processing signals developed by the meter illustrated in FIG. 11A.

FIG. 11B is a schematic diagram of a system for processing signals developed by the photopic and scotopic detectors illustrated in FIG. 11A. Referring to FIGS. 11A and 11B, the signals may be transmitted from connectors 176 and 178 over wires 180, 182 to a microprocessor 196 or other hand-held device. Microprocessor 196 may calculate a flux density of the light inside housing 146 based on the photopic and scotopic response functions. Microprocessor 196 may also calculate a mesopic response based upon the photopic and scotopic responses. The signals may be transmitted by a direct wire connection, or over a network connection such a LAN, an Ethernet connection, a connection over a global information network such as the World Wide Web or the Internet, or a combination of any of them.

If the signals are transmitted over a network connection, a transmitter (not shown) may be coupled to connectors 176, 178 and a receiver (not shown) may be coupled to the computer, hand-held device, or microprocessor 196. The transmitter may be a hardware network adapter used with software to implement standard network communication protocols and to create and manage transfer of signals and other interactions between meter 146 and the computer, hand-held device, or microprocessor 196. The receiver may be a hardware network adapter used with software to implement standard network communication protocols to create and manage reception of messages controlling signal transfer and other interactions between RFD meter 146 and the computer, hand-held device, or microprocessor 196.

Microprocessor 196 or other hand-held device may include, for example, a general purpose computer. Microprocessor 196 may be able to perform the tasks required. Microprocessor 196 may be any type of processing device capable of implementing the steps necessary to perform the various procedures and operations discussed in the specification. Microprocessor 196 may be a general purpose programmable digital device using a stored program.

The computer, hand-held device, or microprocessor 196 may have a video display that displays various information and data to the user. An input device and a pointing device may allow the user of the computer, hand-held device, or microprocessor 196 to enter information and commands to the computer, hand-held device, or microprocessor 196 or system. The input device may be, for example, a keyboard, keypad, handwriting recognition device, or voice recognition device. The pointing device may be, for example, a mouse, track ball, or touch pad. A printer may be coupled to the computer, hand-held device, or microprocessor 196 and may be capable of creating a hard copy of information generated by or used by them. The computer, hand-held device, or microprocessor 196 may include software to perform the necessary calculations.

Embodiments of the present invention may be implemented using a computer-readable medium (also referred to as a processor-readable medium) containing various sets of instructions, code sequences, configuration information, and other data used by a computer, hand-held device, or microprocessor 196, or other processing device. The various information stored on the computer-readable medium may be used to perform various data communication, data processing, and data handling operations, such as those described in the specification. The computer-readable medium may be any type of magnetic optical, or electrical storage medium, including a diskette, magnetic tape, CD-ROM, memory device, or other storage medium.

In an exemplary embodiment, the photopic and scotopic analog signals from connectors 176, 178 are in the range of $10^{-13}$ to $10^{-5}$ amps. Accordingly, the analog signals may be transmitted over wires 180, 182 to amplifiers 184, 186 which amplify and transform the signals to a useful voltage level. The amplified signals are then transmitted to analog-to-digital converters (ADCs) 188, 190 which transform the analog signals into digital signals and transmit the digital signals over wires 192, 194 to a computer, hand-held device, or microprocessor 196. In an exemplary embodiment, ADCs 188, 190 may be successive approximation type analog-to-digital converters.

Feedback loops 198 and 199 are provided from microprocessor 196 to amplifiers 184 and 186, respectively. The feedback loops provide auto-ranging which deals with the large dynamic range of signal levels that may be received from the photopic and scotopic sensors. In an exemplary embodiment, the phototopic signals received at connector 176 and transmitted to amplifier 184 may vary from $10^{-13}$ to $10^{-5}$ amps; the scotopic signals at connector 178 and transmitted to amplifier 186 may vary from $10^{-13}$ to $10^{-5}$ amps. In the configuration shown in FIG. 11B, microprocessor 196 may change the gain of each amplifier 184, 186 to preset levels so that the signals transmitted to the input sides of analog-to-digital converters 188 and 190 are well within the operating limits of ADCs 188, 190. Because microprocessor 196 controls the gain of amplifiers 184, 186, it may apply a correct multiplying factor to the signals transmitted from the output sides of amplifiers 184, 186 to arrive at correctly scaled measured values.

In an alternative embodiment, ADCs 188, 190 may each be integrating ADCs and feedback may be provided from microprocessor 196 to ADCs 188, 190 instead of to amplifiers 184, 186. In such an embodiment, microprocessor 196 may control a variable integration time of each ADC and then scale the signals transmitted from the output side of ADCs 188, 190 by the inverse of the integration time.

Figure 13:
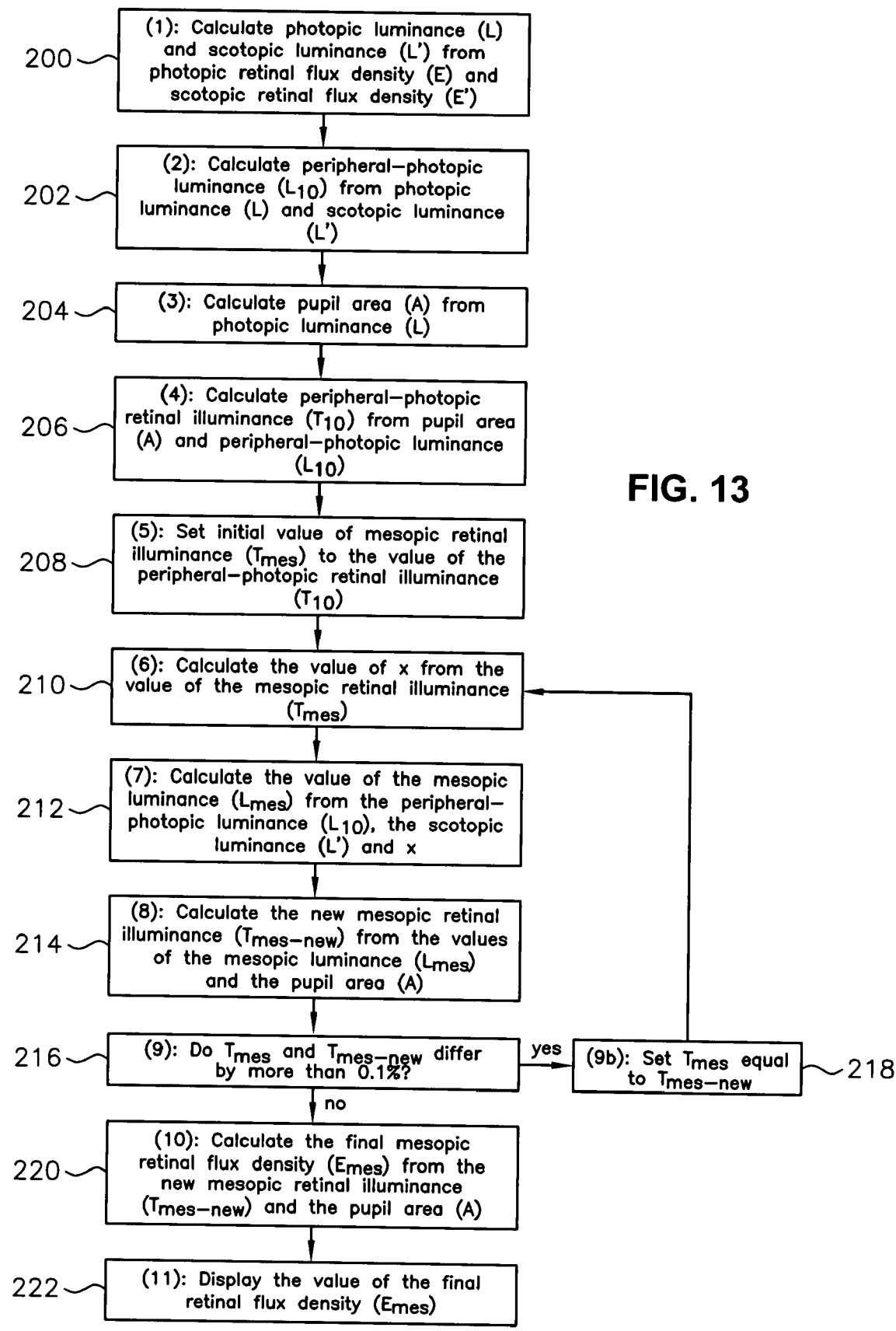
FIG. 13 is a block diagram flow chart illustrating an exemplary embodiment of a method for utilizing the measurements obtained by the meter illustrated in FIG. 11A.

The block diagram shown in FIG. 13 illustrates a series of steps based on a revised algorithm that is, in turn, based on the algorithm in He II. Once light is transmitted to microprocessor 196, the method illustrated in FIG. 13 may calculate mesopic luminance based on the two measured values: the photopic luminance (L) applicable to the cones in an eye and the scotopic luminance (L') applicable to the rods in an eye. When the signals from connectors 176, 178 are received by the computer, hand-held device, or microprocessor 196, a series of calculations may be performed in order to provide an approximation of mesopic flux density.

In the flow chart, values of E, E', and $E_{mes}$ are in lumens per square meter (lm/m$^2$). Values of L, L', and $L_{10}$ are in candelas per square meter (cd/m$^2$). Values of $T_{10}$, $T_{mes}$, and $T_{mes-new}$ are in trolands (Td). Values of A are in square millimeters (mm$^2$). Values of x are unitless; this value is always between 0 and 1 and is an indication of the visual adaptation level. When x=0, the adaptation level is purely scotopic (using rods for vision). When x=1, the adaptation level is purely photopic (using cones for vision). When 0<x<1, x is the relative proportion of cone vision and (1−x) is the relative proportion of rod vision.

Before Step 1 is performed, signals expressing measured photopic retinal flux density (E) and measured scotopic retinal flux density (E') may have been received by microprocessor 196 from meter 146. Then, as shown in Block 200, Step 1, from the measured photopic retinal flux density (E) and the scotopic retinal flux density (E'), the photopic luminance (L) and the scotopic luminance (L') may be calculated using:

a): $L=E/\pi$ b): $L'=E'/\pi'$

Then, as shown in Block 202, Step 2 calculates the peripheral-photopic luminance ($L_{10}$) from the photopic luminance (L) and the scotopic luminance (L'). The calculation is performed using the following approximation:

$L_{10}=0.9822L+0.0397L'$.

This equation accounts for the slightly increased short-wavelength sensitivity of the peripheral cones relative to the foveal (in the central retina) cones, because the photopic luminance (L) applies only to the foveal cones. The value calculated in Step 2 is an approximation of a peripheral-photopic luminance of light incident on a combination of foveal and peripheral cones of a retina.

In Step 3, Block 204, the pupil area A of the mimicked eye receiving the light is calculated from the phototopic luminance (L) according to the equation $A=\pi\{5-3\tan h[0.41\log(L)]\}^2/4$, where π is 3.14159, tanh is the hyperbolic tangent, and log is the base-10 logarithm.

In Step 4, Block 206, the peripheral-photopic retinal illuminance ($T_{10}$) is calculated from the pupil area (A) and the peripheral-photopic luminance ($L_{10}$) according to the equation:

$T_{10}=A L_{10}$.

In Step 5, Block 208, the initial value of the mesopic retinal illuminance ($T_{mes}$) is set to the value of the peripheral-photopic retinal illuminance ($T_{10}$). That is, $T_{mes}=T_{10}$.

In Step 6, Block 210, if the value of the mesopic retinal illuminance ($T_{mes}$) is less than 21 Td, the value of x is calculated using the mesopic retinal illuminance ($T_{mes}$) in accordance with the equation:

$x=0.115(T_{mes}+0.006)^{0.71}$.

On the other hand, if the value of the mesopic retinal illuminance ($T_{mes}$) is equal to or greater than 21 Td, x is set to equal 1.

In Step 7, Block 212, the value of the mesopic luminance ($L_{mes}$) is calculated from the values of the peripheral-photopic luminance ($L_{10}$), the scotopic luminance (L'), and x according to the equation:

$L_{mes}=(1700-1017x)[xL_{10}/683+(1-x)L'/1700]$.

In Step 8, Block 214, a new mesopic retinal illuminance ($T_{mes-new}$) is calculated from the values of the pupil area (A) and the mesopic luminance ($L_{mes}$):

$T_{mes-new}=A L_{mes}$.

In Step 9, Block 216, the method determines if the values of $T_{mes}$ and $T_{mes-new}$ differ by more than 0.1%. If the values do differ by more than 0.1%, Block 218 (Step 9b) shows that the value of $T_{mes}$ is set to equal the value of $T_{mes-new}$ and the process returns to Step 6, Block 208. The return to Step 6 reflects an iterative process that continues until the comparison illustrated in Block 216 determines that the values of $T_{mes}$ and $T_{mes-new}$ no longer differ by more than 0.1%. Accordingly, if the process returns to Step 6 in Block 210, Steps 6 to 9, Blocks 210 to 216 and, if necessary, Block 218 are repeated until the values of $T_{mes}$ and $T_{mes-new}$ no longer differ by more than 0.1%. Whenever the comparison made in Step 9, Block 216, determines that the values of $T_{mes}$ and $T_{mes-new}$ no longer differ by more than 0.1%, the process proceeds to step 10, Block 220.

In Step 10, Block 220, the final mesopic retinal flux density value ($E_{mes}$) is calculated from the new mesopic retinal illuminance ($T_{mes-new}$) and the pupil area (A) according to the equation:

$E_{mes}=\pi T_{mes-new}/A$.

The value calculated in Step 10 is an approximation of a mesopic flux density of light incident on a combination of cones and rods of a retina.

In Step 11, Block 222, the value of the final mesopic retinal flux density ($E_{mes}$) is displayed. It may be displayed as a display on meter 146 or on the computer, hand-held device, or microprocessor 196 in ways that are known to those skilled in the art.

Thus, meter 146 uses the photopic and scotopic responses, $V_\lambda$, and $V'_\lambda$, to produce values of E and E'. In an exemplary embodiment, the $V_\lambda$, and $V'_\lambda$ functions may not change. E mesopic ($E_{mes}$) may tend to look either more like $V_\lambda$ or more like $V'_\lambda$ depending on the light level that is incident upon meter 146. If the light is at a high light level, meter 146 is working only with the photopic function and that function may not change. When the light is at a very low level, meter 146 may operate at the other end of the range and the scotopic function may not change. By then following the algorithm illustrated in FIG. 13, the system can calculate a mesopic function by calculating $L_{10}$ followed by the additional calculations identified in FIG. 13.

In an alternative embodiment, baffle 150 may be removed from meter 146 and meter 146 may then be used as a standard illuminance meter, measuring only the photopic response of light that is incident on the meter. Because meter 146 may be designed to be small enough to be portable, the user may be able to carry only one meter instead of multiple meters. Accordingly, the baffle may be on or off depending on what kind of light measurement the user wants to obtain.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention.

What is claimed:

1. A system for approximating flux density of light on a retina, the system comprising:
    a housing defining an inside and having an opening allowing light to pass to the inside of the housing;
    a baffle coupled to the housing, the baffle replicating the facial cutoff function for the light passing to the inside of the housing;
    a first detector positioned to detect the light inside the housing, the first detector producing a photopic spectral response function of the light inside the housing that approximately replicates a spectral response of foveal cones;
    a second detector positioned to detect the light inside the housing, the second detector producing a scotopic spectral response function of the light inside the housing that approximately replicates a spectral response of rods in the retina; and
    a processor coupled to the first and second detectors, the processor being configured to calculate a flux density of the light inside the housing based on the photopic and scotopic spectral response functions.

2. The system of claim 1, wherein the first detector includes a first filter producing the photopic spectral response function and the second detector includes a second filter producing the scotopic spectral response function.

3. The system of claim 2, wherein the first detector includes a first photocell producing a first signal weighted by the photopic spectral response function and the second detector includes a second photocell producing a second signal weighted by the scotopic spectral response function.

4. The system of claim 3, further comprising a signal transmission means for transmitting the first and second signals to the processor.

5. The system of claim 1, wherein the first detector includes a first photocell producing a first signal weighted by the photopic spectral response function and the second detector includes a second photocell producing a second signal weighted by the scotopic spectral response function.

6. A system for approximating a flux density of light on a retina, the system comprising:
    a housing defining an inside and having an opening allowing light to pass to the inside of the housing;
    a baffle coupled to the housing, the baffle replicating a retinal spatial response for the light passing to the inside of the housing;
    a first detector positioned to detect the light inside the housing, the first detector producing a first signal approximately replicating a spectral response of cones in the retina to the light inside the housing;
    a second detector positioned to detect the light inside the housing, the second detector producing a second signal approximately replicating a spectral response of rods in the retina to the light inside the housing; and
    a processor coupled to the first and second detectors for receiving the first and second signals, the processor being configured to calculate a flux density of the light inside the housing based on the first and second signals.

7. The system of claim 6, further comprising a beam splitter for transmitting the light inside the housing into at least two directions.

8. The system of claim 6, further comprising a beam splitter for transmitting a first portion of the light inside the housing toward the first detector and for transmitting a second portion of the light inside the housing toward the second detector.

9. The system of claim 6, further comprising a lens coupled to the housing for focusing the light inside the housing, wherein the baffle surrounds the lens.

10. The system of claim 6, wherein the first detector includes a first filter producing a photopic spectral response function and the second detector includes a second filter producing a scotopic spectral response function.

11. The system of claim 10, wherein the first detector includes a first photocell producing a first signal weighted by the photopic spectral response function and the second detector includes a second photocell producing a second signal weighted by the scotopic spectral response function.

12. The system of claim 6, wherein the first detector includes a first photocell producing a first signal weighted by a photopic spectral response function and the second detector includes a second photocell producing a second signal weighted by a scotopic spectral response function.

13. A method of approximating a peripheral-photopic luminance of light incident on a combination of foveal and peripheral cones of a retina, the method comprising the steps of:
    producing a first signal weighted by a spectral response of the foveal cones to the light and proportional to a first flux density of the light received by the foveal cones;
    producing a second signal weighted by a spectral response of rods in the retina to the light and proportional to a second flux density of the light received by the rods; and
    applying a function to the first and second signals to approximate the peripheral-photopic response.

14. The method of claim 13, wherein the function comprises the steps of:

calculating a first luminance on the foveal cones based upon the first flux density;

calculating a second luminance on the rods based upon the second flux density; and calculating the peripheral-photopic luminance based upon the first and second luminances.

15. A method of approximating a mesopic retinal flux density of light incident on a combination of cones and rods of a retina, the method comprising the steps of:

producing a first signal weighted by a spectral response of the cones to the light and proportional to a first flux density of the light received by the cones;

producing a second signal weighted by a spectral response of the rods to the light and proportional to a second flux density of the light received by the rods; and applying an algorithm to the first and second signals to determine the mesopic retinal flux density.

16. The method of claim 15, further comprising the steps of:

calculating a first photopic luminance based upon the first flux density;

calculating a second scotopic luminance based upon the second flux density;

calculating a third peripheral-photopic luminance based upon the first and second luminances; and calculating the mesopic flux density based upon the third peripheral-photopic luminance.

17. A machine-readable storage medium containing a set of instructions for a general purpose computer, the set of instructions implementing the steps of:

producing a first signal weighted by a spectral response of foveal cones to light and proportional to a first flux density of the light received by the foveal cones;

producing a second signal weighted by a spectral response of rods in the retina to the light and proportional to a second flux density of the light received by the rods; and applying a function to the first and second signals to approximate a peripheral-photopic response.

18. A machine-readable storage medium containing a set of instructions for a general purpose computer, the set of instructions implementing the steps of:

producing a first signal weighted by a spectral response of retinal cones to light and proportional to a first flux density of the light received by the retinal cones;

producing a second signal weighted by a spectral response of retinal rods to the light and proportional to a second flux density of the light received by the retinal rods; and applying an algorithm to the first and second signals to determine a mesopic retinal flux density.

* * * * *